United States Patent
Deng et al.

(10) Patent No.: US 7,915,404 B2
(45) Date of Patent: Mar. 29, 2011

(54) METHODS FOR THE PREPARATION OF PYRAZOLE-CONTAINING COMPOUNDS

(75) Inventors: Xiaohu Deng, San Diego, CA (US);
Jimmy T. Liang, San Diego, CA (US);
Neelakandha Mani, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 896 days.

(21) Appl. No.: 11/744,340

(22) Filed: May 4, 2007

(65) Prior Publication Data
US 2007/0260057 A1    Nov. 8, 2007

Related U.S. Application Data

(60) Provisional application No. 60/746,497, filed on May 5, 2006.

(51) Int. Cl.
*C07D 487/04*  (2006.01)
(52) U.S. Cl. ........................................ 540/578
(58) Field of Classification Search .................. 540/578
See application file for complete search history.

(56) References Cited

U.S. PATENT DOCUMENTS
2005/0119295 A1    6/2005   Carruthers et al.

FOREIGN PATENT DOCUMENTS
WO    WO 2005 040169 A2    5/2005
WO    WO 2008 013556 A1    1/2008

OTHER PUBLICATIONS

International Search Report for Corresponding PCT/US2007/068210 Dated Nov. 21, 2007 4 Pgs.
Abdallah-El Ayoubi, S. et al. Minute Synthesis of Electrophilic Alkenes under Microwave Irradiation. Synthesis, 1994, 3, 258-260.
Alexakis, A. et al. Diamine-Catalyzed Asymmetric Michael Additions of Aldehydes and Ketones to Nitrostyrene. Org. Lett. 2002, 4(21), 3611-3614.
Bardakos, V. et al. Enehydrazines. 10. Aliphatic enehydrazones. Chem. Ber. 1975, 108(7), 2161-2170.
Barnes, D.M. et al. Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram. J. Am. Chem. Soc. 2002, 124(44), 13097-13105.
Baumes, R. et al. Condensation of aldehyde methylhydrazones with acetylenic esters: Synthesis of carbomethoxypyrazolines. Bull. Soc. Chim. Fr. 1976(1-2,Pt.2), 260-264.
Brimble, M.A. et al. Synthesis of bicyclic pyrazinones via addition of heterocyclic amines to a nitro-alkene. Tetrahedron 1994, 50(16), 4887-4896.
de Mico, A. et al. A Versatile and Highly Selective Hypervalent Iodine (III)/2,2,6,6-Tetramethyl-1-piperidinyloxyl-Mediated Oxidation of Alcohols to Carbonyl Compounds. J. Org. Chem. 1997 62(20), 6974-6977.
Deng, X. et al. Reaction of N-Monosubstituted Hydrazones with Nitroolefins: A Novel Regioselective Pyrazole Synthesis. Org. Lett. 2006, 8(16), 3505-3508.
Deng, X. et al. Regioselective Synthesis of 1,3,5-Tri- and 1,3,4,5-Tetrasubstituted Pyrazoles from N-Arylhydrazones and Nitroolefins. J. Org. Chem. 2008, in press.
Deng, X. et al. Base-Mediated Reaction of Hydrazones and Nitroolefins with a Reversed Regioselectivity: A Novel Synthesis of 1,3,4-Trisubstituted Pyrazoles. Org. Lett. 2008, in press.
Denmark, S.E. et al. Intramolecular [4+2] cycloadditions of nitroalkenes with olefins. J. Am. Chem. Soc. 1986, 108(6), 1306-1307.
Denmark, S.E. et al. α-Nitro keto hydrazone and keto imine dianions. Synthetic equivalents for the nitroalkene d3 synthon. J. Org. Chem. 1988, 53(6), 1251-1263.
Denmark, S.E. et al. Intramolecular [4+2]-cycloadditions of nitroalkenes with olefins. 2. Tetrahedron 1990, 46(21), 7373-7392.
Elguero, et al. Comp. Heterocycl. Chem. 1984, vol. 5, pp. 167 and 273-302.
Elguero et al Comp Heterocyl Chem II 1996 vol. 3 pp. 1, and 66-75.
Elguero et al. Targets in Heterocyclic Systems 2002 vol. 6 pp. 52-98.
Escribano, F.C. et al. Heterocycle formation from 1,3-dinitroalkanes. A novel pyrazole synthesis. Tetrahedron Lett. 1988, 29(46), 6001-6004.
Gomez-Sanchez, A. et al. Furan and Pyrrole Formation from 2-Nitro-1-phenylpropene and Acetoacetic Esters. J. Chem. Res. (S) 1985, 318-319.
Gomez Guillen, M. et al. Reaction of D-Galactose Phenylhydrazone with Nitroalkenes: Synthesis of Pentahydroxypentylpyrazoles. Carbohydr. Res. 1988, 138, 1-17.
Gomez-Guillen, M. et al. New Pentahydroxypentylpyrazoles from Reactions of D-Mannose and D-Galactose Methylhydrazones with Nitroalkenes. Carbohydr. Res. 1989, 189, 349-358.
Griesser, H. et al. 3-Nitropropanal, 3-Nitropropanol, and 3-Nitropropanal Dimethyl Acetal. Org. Synth. 2000, 77, 236-243.
Grigg, R. et al. X=Y-ZH Systems as potential 1,3-dipoles : Part 13. Prototropic generation of azomethine imines from hydrazones. Tetrahedron 1987, 43(24), 5873-5886.
Grigg, R. et al. X=Y-ZH Systems as potential 1,3-dipoles. Tetrahedron Lett. 1978, 19(31), 2827-2830.
Hori, K. et al. Theoretical and experimental study on the stereoselectivity of Michael addition of alkoxide anion to nitro olefin. J. Org. Chem. 1990, 55(23), 5900-5905.
Kamimura, A. et al. Anti-selective Michael addition of thiols and their analogs to nitro olefins. J. Org. Chem. 1990, 55(8), 2437-2442.
Kobayashi, S. et al. Lewis acid-mediated [3+2] cycloaddition between hydrazones and olefins. Tetrahedron Lett. 2003, 44(16), 3351-3354.
Le Fevre, G. et al. Addition d'hydrazone aux oléfines en milieu acide: cycloaddition polaire cationique [3⁺+2]. Tetrahedron 1979, 35(15), 1821-1824.
Le Fevre, G. et al. Addition de phénylhydrazones aux oléfines en milieu neuter. Tetrahedron 1980, 36(7), 887-891.

(Continued)

*Primary Examiner* — Brenda L Coleman
(74) *Attorney, Agent, or Firm* — Michael J. Atkins

(57) ABSTRACT

The present invention is directed to novel processes for the preparation of fused pyrazole compounds, useful for the treatment of disorders and conditions mediated by serotonin receptor activity.

21 Claims, No Drawings

OTHER PUBLICATIONS

Liang. et al. A Novel Scale Up Route to 3-(4-Fluoro-phenyl)-2-isopropyl-2,4,5,6,7,8-hexahydro-1,2,6-triaza-azulene, a Serotonin Modulator. Abstract for ACS Fall 2008 National Meeting, Philadelphia, PA, to be presented Aug. 2008.

Lim, S. et al. Reaction of cyclohexanones imines with substituted nitroolefins. New synthesis of tetrahydroindole derivatives. Tetrahedron Lett. 1999, 40(22), 4177-4180.

Meyer, H. Pyrrole durch cyclisierende Michael-Addition von Enaminen. Justus Liebigs Ann. Chem. 1981,1534-1544.

Miller, R.D. et al. The synthesis of electron donor-acceptor substituted pyrazoles. J. Heterocyclic Chem. 1993, 30(3), 755-763.

Ohrlein, R. et al. 3-Nitropropanal and 3-Nitropropanol: Preparation of the Parent Compounds and Derivatives. Synthesis, 1986, 7, 535-537.

Parham, W.E. et al. Reactions of Diazo Compounds with Nitroölefins. I. The Preparation of Pyrazoles. J. Am. Chem. Soc. 1950, 72(9), 3843-3846.

Penning, T.D. et al. Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrazol-1-yl]benzenesulfonamide (SC-58635, Celecoxib). J. Med. Chem. 1997, 40(9), 1347-1365.

Ranu, B.C. et al. Synthesis of alkyl-substituted pyrroles by three-component coupling of carbonyl compound, amine and nitro-alkane/alkene on a solid surface of silica gel/alumina under microwave irradiation. Tetrahedron 2001, 57(22), 4767-4773.

Schmidt, R.R. Polar Cycloadditions. Angew. Chem., Int. Ed. Engl. 1973, 12(3), 212-224.

Shiraishi, H. et al. Preparation of Substituted Alkylpyrroles via Samarium-Catalyzed Three-Component Coupling Reaction of Aldehydes, Amines, and Nitroalkanes. J. Org. Chem. 1998 63(18), 6234-6238.

Shiraishi, H. et al. Regioselective synthesis of alkylpyrroles from imines and nitroalkenes by lanthanide compounds. Tetrahedron 1999, 55(49), 13957-13964.

Snider, B.B. et al. Reactions of Phenylhydrazones with Electron-Deficient Alkenes. J. Org. Chem. 1979, 44(2), 218-221.

Stott et al "One-Dimensional NOE Experiments Using Pulsed Field Gradients" J Magn Reson 1997 vol. 125 pp. 302-324.

Terrett, N.K. et al. Sildenafil (VIAGRA™), a potent and selective inhibitor of type 5 cGMP phosphodiesterase with utility for the treatment of male erectile dysfunction. Bioorg. Med. Chem. Lett. 1996, 6(15), 1819-1824.

Tsao, Y.-Y. et al. A new reagent for the detection of nitrous acid in drinking water. J. Chin. Chem. Soc. (Peking) 1937, 5, 55-59, English language abstract.

Yasuhara, T. et al. Total Synthesis of ($\pm$)-$\alpha$- and $\beta$-Lycoranes by Sequential Chemoselective Conjugate Addition-Stereoselective Nitro-Michael Cyclization of an $\omega$-Nitro-$\alpha,\beta,\psi,\omega$-unsaturated Ester. Org. Lett. 2003, 5(7), 1123-1126.

Yasuhara, T. et al. Efficient synthesis of ($\pm$)-$\gamma$-lycorane employing stereoselective conjugate addition to nitroolefin. Tetrahedron Lett. 2004, 45(15), 3043-3045.

Comprehensive Heterocyclic Chemistry II—A Review of The Literature 1983-1995 1996, pp. 817-932 Katritzky Rees ScrivenEds.

METHODS FOR THE PREPARATION OF PYRAZOLE-CONTAINING COMPOUNDS

CROSS-REFERENCE TO RELATED APPLICATIONS

This application claims the benefit of U.S. Provisional Application 60/746,497, filed May 5, 2006, which is hereby incorporated by reference in its entirety.

FIELD OF THE INVENTION

The present invention is directed to processes for the preparation of fused pyrazole compounds, useful for the treatment of disease states mediated by serotonin receptor activity.

BACKGROUND OF THE INVENTION

The present invention is directed to processes for the preparation of compounds of Formula (I):

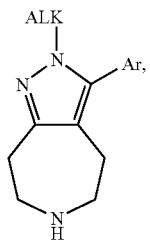

(I)

where Ar and ALK are defined as below. Compounds of Formula (I) are modulators of serotonin receptors, and are useful in methods for treating or preventing diseases and conditions mediated by serotonin receptors, particularly the 5HT$_7$ and/or 5HT$_2$ receptor subtypes. Said compounds were disclosed in US Pat. Appl. Publ. US 20050119295, published Jun. 2, 2005, which is hereby incorporated by reference. More particularly, the compounds are useful for treating or preventing CNS disorders, such as sleep disorders, depression/anxiety, generalized anxiety disorder, schizophrenia, bipolar disorders, psychotic disorders, obsessive-compulsive disorder, mood disorders, post-traumatic stress and other stress-related disorders, migraine, pain, eating disorders, obesity, sexual dysfunction, metabolic disturbances, hormonal imbalance, alcohol abuse, addictive disorders, nausea, inflammation, centrally mediated hypertension, sleep/wake disturbances, jetlag, and circadian rhythm abnormalities. The compounds may also be used in the treatment and prevention of hypotension, peripheral vascular disorders, cardiovascular shock, renal disorders, gastric motility, diarrhea, spastic colon, irritable bowel disorders, ischemias, septic shock, urinary incontinence, and other disorders related to the gastrointestinal and vascular systems. In addition, the compounds may be used in the treatment or prevention of a range of ocular disorders including glaucoma, optic neuritis, diabetic retinopathy, retinal edema, and age-related macular degeneration.

Substituted pyrazoles are important synthetic targets in the pharmaceutical industry, as the pyrazole motif makes of the core structure of numerous biologically active compounds (Elguero, J.; Goya, P.; Jagerovic, N.; Silva, A. M. S. *Targets in Heterocyclic Systems* 2002, 6, 52-98) including marketed drugs such as sildenafil (Terrett, N. K. et al. *Bioorg. Med. Chem. Lett.* 1996, 6, 1819-1824) and celecoxib (Penning, T. D. et al. *J. Med. Chem.* 1997, 40, 1347-1365). Pyrazoles are often prepared by the reaction of hydrazines with 1,3-dicarbonyl compounds or their equivalents, such as α,β-ethynylketones or esters. These condensation reactions generally result in mixtures of regioisomers, which complicates isolation and purification processes. Cyclization reactions of 1,3-dipoles such as deazoalkanes or nitrilimines with olefins has also been used, but these reactions often suffer from low yields and harsh conditions (Elguero, J. Comp. Heterocycl. Chem. 1984, 5, 167; Elguero, J. Comp. Heterocycl. Chem. II 1996, 3, 1-75 and 817-932, and references cited therein). These processes are therefore unsuitable for large scale production of substituted pyrazoles.

Thus, there remains a need for a process for the preparation of fused pyrazole compounds, wherein a pyrazole regioisomer of Formula (I), as hereinafter defined, is preferentially prepared.

To this end, condensation of nitroalkenes with hydrazones was investigated. Nitroalkenes have been used in the formation of other heterocyclic systems (Meyer, H. Justus Liebigs Ann. Chem. 1981, 1534-1544; Gomez-Sanchez, A. et al. J. Chem. Res. (S) 1985, 318-319). However, the reaction between a hydrazone and a nitroalkene, neat or in Et$_2$O, was shown to produce only nitro-pyrazolidine products, which further oxidized upon standing to give nitro-pyrazoles (Snider, B. B. et al. J. Org. Chem. 1979, 44(2), 218-221; Equation 1). Snider and co-workers noted that despite their investigation of a variety of conditions, they were unable to obtain any other products from the reaction.

In a subsequent report, reaction of a hydrazone with a nitroolefin in a DMF/H$_2$O mixture did form a pyrazole without the nitro substituent (Gomez Guillen, M.; Jimenez, J. L. C. Carbohydrate Res. 1988, 180, 1-17; Equation 2).

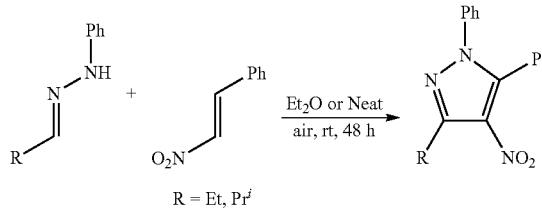

(1)

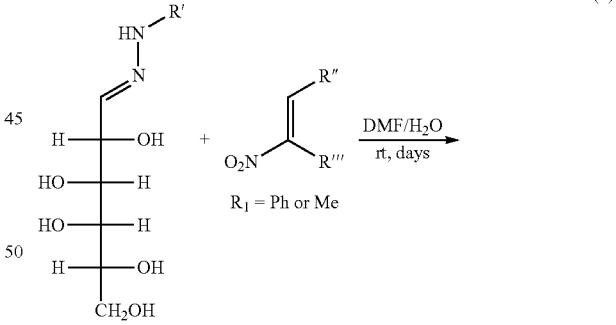

(2)

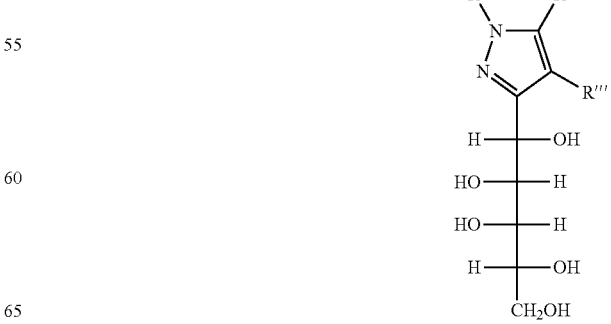

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety.

SUMMARY OF THE INVENTION

Relative to existing methods, embodiments of the synthetic route according to this invention provide a concise methodology that is suitable for readily making a range of structurally related substituted pyrazole analogs.

In one general aspect, the present invention relates to a method of making a compound of Formula (I):

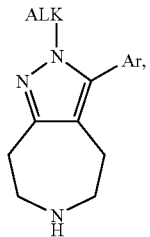
(I)

or an enantiomer, diastereomer, hydrate, solvate, or pharmaceutically acceptable salt thereof;
comprising reacting a compound of formula (IV):

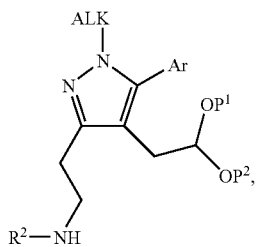
(IV)

with an acid under reducing conditions, in a non-basic organic solvent, at a temperature between about room temperature and the reflux temperature of the solvent, to provide the compound of Formula (I),
wherein
Ar is:
A) phenyl, optionally mono-, di-, or tri-substituted with $R^a$ or di-substituted on adjacent carbons with —$OC_{1-4}$alkyleneO—;
each $R^a$ is independently selected from the group consisting of —OH, —$C_{1-6}$alkyl, —$OC_{1-6}$alkyl, —CN, —$NO_2$, —$N(R^b)R^c$, —$C(O)N(R^b)R^c$, —$N(R^d)C(O)R^d$, —$N(R^d)SO_2C_{1-6}$alkyl, —$C(O)C_{1-6}$alkyl, —$S(O)_{0-2}$—$C_{1-6}$alkyl, —$SO_2N(R^b)R^c$, —$SCF_3$, halo, —$CF_3$, —$OCF_3$, —COOH, —$COOC_{1-6}$alkyl, and tetrazolyl;
where $R^b$ and $R^c$ are each independently —H or —$C_{1-6}$alkyl;
where $R^d$ is —H or —$C_{1-6}$alkyl;
B) a monocyclic aromatic hydrocarbon group having five ring atoms, having a carbon atom which is the point of attachment, having one carbon atom replaced by >O, >S, >NH, or >N($C_{1-4}$alkyl), having up to one additional carbon atom optionally replaced by —N=, and optionally mono- or di-substituted with $R^a$; or
C) a monocyclic aromatic hydrocarbon group having six ring atoms, having a carbon atom which is the point of attachment, having one or two carbon atoms replaced by —N=, and optionally mono- or di-substituted with $R^a$;
ALK is:
i) $C_{1-7}$alkyl, optionally substituted with $R^e$;
where $R^e$ is selected from the group consisting of —OH, —$OC_{1-6}$alkyl, —CN, —$N(R^f)R^g$, —$C(O)N(R^f)R^g$, —$N(R^h)C(O)R^h$, —$N(R^h)SO_2C_{1-6}$alkyl, —$C(O)C_{1-6}$alkyl, —$S(O)_{0-2}$—$C_{1-6}$alkyl, —$SO_2N(R^f)R^g$, fluoro, —$CF_3$, —COOH, and —$COOC_{1-6}$alkyl;
where $R^f$ and $R^g$ are each independently —H or —$C_{1-6}$alkyl; and
where $R^h$ is —H or —$C_{1-6}$alkyl;
ii) a cycloalkyl ring, optionally mono-, di-, or tri-substituted with $R^e$ or $C_{1-6}$alkyl;
iii) phenyl, optionally mono- di-, or tri-substituted with $R^e$; or
iv) —$C_{1-2}$alkyl-CYC;
wherein CYC is selected from the group consisting of:
a) a phenyl or naphthyl group, optionally mono-, di-, or tri-substituted with $R^h$ or di-substituted on adjacent carbons with —$OC_{1-4}$alkyleneO—;
each $R^h$ is independently selected from the group consisting of —OH, —$C_{1-6}$alkyl, —$OC_{1-6}$alkyl, —CN, —$NO_2$, —$N(R^i)R^j$, —$C(O)N(R^i)R^j$, —$N(R^i)C(O)R^j$, —$N(R^i)SO_2C_{1-6}$alkyl, —$C(O)C_{1-6}$alkyl, —$S(O)_{0-2}$—$C_{1-6}$alkyl, —$SO_2N(R^i)R^j$, —$SCF_3$, halo, —$CF_3$, —$OCF_3$, —COOH, and —$COOC_{1-6}$alkyl;
where $R^i$ and $R^j$ are each independently —H or —$C_{1-6}$alkyl; and
b) a monocyclic aromatic hydrocarbon group having five ring atoms, having a carbon atom which is the point of attachment, having one carbon atom replaced by >O, >S, >NH, or >N($C_{1-4}$alkyl), having up to one additional carbon atoms optionally replaced by —N=, optionally mono- or di-substituted with $R^h$;
c) a monocyclic aromatic hydrocarbon group having six ring atoms, having a carbon atom which is the point of attachment, having one or two carbon atoms replaced by —N=, optionally mono- or di-substituted with $R^h$; and
d) a cycloalkyl ring, having 0, 1, or 2 unsaturated bonds, optionally mono- or di-substituted with $R^h$;
$R^2$ is —$CO_2R^{10}$ or a benzyl group unsubstituted or substituted with one or two —$OCH_3$ substituents;
where $R^{10}$ is methyl, ethyl, 2-trimethylsilylethyl, 2-phenylethyl, 1-(1-adamantyl)-1-methylethyl, t-butyl, 1-adamantyl, vinyl, allyl, benzyl, p-methoxybenzyl, p-nitrobenzyl, p-chlorobenzyl, 2,4-dichlorobenzyl, or diphenylmethyl; and
$P^1$ and $P^2$ are each independently —$C_{1-4}$alkyl, or, alternatively, $P^1$ and $P^2$ taken together form —$(CH_2)_{2-3}$—.

The method of making a compound of Formula (I) further comprises: reacting a hydrazone of formula (II):

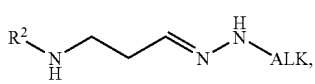
(II)

with a nitroolefin of formula (III):

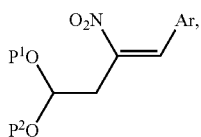

(III)

in the presence of oxygen, in an organic solvent, at a temperature between about room temperature and the reflux temperature of the solvent, to form the compound of formula (IV), wherein $R^2$, Ar, ALK, $P^1$, and $P^2$ are defined as above.

The present invention is further directed to compounds of formulae (IV), (II), and (III):

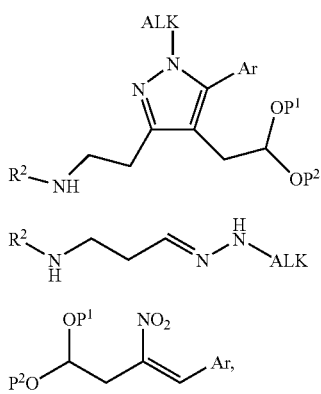

(IV)

(II)

(III)

wherein $R^2$, Ar, ALK, $P^1$, and $P^2$ are defined as above. Compounds of formulae (IV), (II), and (III) are useful in the preparation of compounds of Formula (I).

The present invention is further directed to a method of making a compound of Formula (XVI):

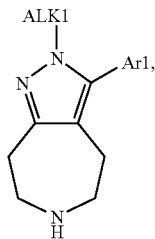

(XVI)

or an enantiomer, diastereomer, hydrate, solvate, or pharmaceutically acceptable salt thereof;
comprising reacting a compound of formula (XV):

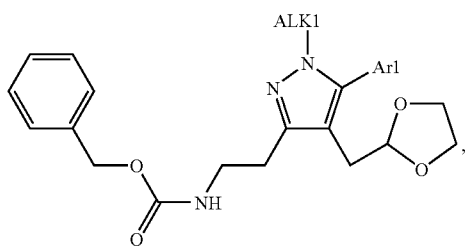

(XV)

with an acid under reducing conditions, in a non-basic organic solvent, to provide the compound of Formula (XVI), wherein
ALK1 is isopropyl or cyclopropyl; and
Ar1 is 4-fluorophenyl.

The present invention is further directed to a compound of Formula (I) prepared according to any of the processes disclosed herein.

Illustrative of the invention is a pharmaceutical composition comprising a pharmaceutically acceptable carrier and a compound of Formula (I) prepared according to any of the processes described herein. An illustration of the invention is a pharmaceutical composition comprising a) a compound of Formula (I) prepared according to any of the processes described herein, and b) a pharmaceutically acceptable carrier. Illustrating the invention is a process for making a pharmaceutical composition comprising mixing a compound of Formula (I) prepared according to any of the processes described herein and a pharmaceutically acceptable carrier.

Exemplifying the invention are methods of treating or preventing a disorder mediated by the serotonin receptor, preferably, the $5HT_7$ and/or $5HT_2$ receptors, wherein said disorder is selected from the group consisting of sleep disorders, depression/anxiety, generalized anxiety disorder, schizophrenia, bipolar disorders, psychotic disorders, obsessive-compulsive disorder, mood disorders, post-traumatic stress and other stress-related disorders, migraine, pain, eating disorders, obesity, sexual dysfunction, metabolic disturbances, hormonal imbalance, alcohol abuse, addictive disorders, nausea, inflammation, centrally mediated hypertension, sleep/wake disturbances, jetlag, circadian rhythm abnormalities, hypotension, peripheral vascular disorders, cardiovascular shock, renal disorders, gastric motility, diarrhea, spastic colon, irritable bowel disorders, ischemias, septic shock, urinary incontinence, other disorders related to the gastrointestinal and vascular systems, and ocular disorders including glaucoma, optic neuritis, diabetic retinopathy, retinal edema, and age-related macular degeneration, in a subject in need thereof comprising administering to the subject a therapeutically effective amount of any of the compounds of Formula (I) or pharmaceutical compositions comprising a compound of Formula (I) as described above.

DETAILED DESCRIPTION

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

As used herein, unless otherwise noted, "halo" shall mean chlorine, bromine, fluorine and iodine.

As used herein, the term "alkyl", whether used alone or as part of a substituent group, include straight and branched alkyl chain of the specified number of carbon atoms. For example, alkyl radicals include methyl (Me), ethyl (Et), propyl (Pr), isopropyl (iPr), butyl (Bu), isobutyl, sec-butyl, t-butyl, pentyl and the like.

As used herein, unless otherwise noted, the term "alkylene" refers to a biradical substituent formed from an alkyl group, as defined herein, in which the biradical is formed by the removal of two hydrogen atoms.

Unless otherwise noted, the term "cycloalkyl" as used herein represents a stable three to eight membered monocyclic ring structure consisting of saturated carbon atoms. Suitable examples include cyclopropyl, cyclobutyl, cyclopentyl, cyclohexyl, cycloheptyl and cyclooctyl.

The term "acid" as used herein represents a protic acid of a pH below about 3, including, but not limited to, TFA, HCl, and $H_2SO_4$.

The term "reducing conditions" as used herein represents:
1) a reducing agent (such as $Et_3SiH$, $NaB(OAc)_3H$, NaCNBH$_3$, and the like), or
2) a hydrogen donor (such as $H_2$, cyclohexene, ammonium formate, formic acid, and the like) and a catalyst (such as palladium on carbon (Pd/C), palladium black (Pd-black), $Pd(OH)_2$, platinum on carbon, Raney nickel, ruthenium black, and the like).

The term "non-basic organic solvent", as used herein, means an organic solvent with a pH less than or equal to 7.

The term "regioisomeric excess", as used herein, refers to the production of regioisomeric products in unequal amounts. As conventionally used, regioisomeric excess means herein the differential of regioisomers produced in a reaction, ($F_{(a)}-F_{(b)}$), where $F_{(a)}$ denotes mole fraction (or mass fraction) of a first regioisomer (a), $F_{(b)}$ denotes mole fraction (or mass fraction) of any other regioisomers (b), and $F_{(a)}+F_{(b)}=1$. When given as a percentage, enantiomeric excess is $100 \cdot |F_{(a)}-F_{(b)}|$.

The following abbreviations or acronyms are used throughout the specification, and are defined as follows:

| Abbreviation or Acronym | Chemical Name |
| --- | --- |
| AcOH | Acetic acid |
| Boc | tert-Butoxycarbonyl |
| Cbz | Benzyloxycarbonyl |
| DCM | Dichloromethane |
| DMF | N,N-Dimethylformamide |
| $Et_3N$ | Triethylamine |
| $Et_2O$ | Diethyl ether |
| EtOAc | Ethyl acetate |
| $Et_3SiH$ | Triethylsilane |
| HPLC | High performace liquid chromatography |
| $iPr_2NEt$ | N,N-diisopropylethylamine |
| MTBE | Methyl tert-butyl ether |
| Ph | Phenyl |
| TFA | Trifluoroacetic acid |
| THF | Tetrahydrofuran |

It is understood that some compounds referred to herein are chiral and/or have geometric isomeric centers, for example E- and Z-isomers. The present invention encompasses all such optical isomers, including diastereomers and racemic mixtures, atropisomers, and geometric isomers, and mixtures thereof, that possess the activity that characterizes the compounds of this invention. In addition, certain compounds referred to herein can exist in solvated as well as unsolvated forms. It is understood that this invention encompasses all such solvated and unsolvated forms that possess the activity that characterizes the compounds of this invention.

Compounds according to the present invention that have been modified to be detectable by some analytic technique are also within the scope of this invention. The compounds of the present invention may be labeled with radioactive elements such as $^{125}I$, $^{18}F$, $^{11}C$, $^{64}Cu$, and the like for use in imaging or for radioactive treatment of patients. An example of such compounds is an isotopically labeled compound, such as an $^{18}F$ isotopically labeled compound that may be used as a probe in detection and/or imaging techniques, such as positron emission tomography (PET) and single-photon emission computed tomography (SPECT). Preferably, compounds of the present invention labeled with $^{18}F$ or $^{11}C$ may be used as a PET molecular probe for studying serotonin-mediated disorders. Another example of such compounds is an isotopically labeled compound, such as a deuterium and/or tritium labeled compound, that may be used in reaction kinetic studies. The compounds described herein may be reacted with an appropriate functionalized radioactive reagents using conventional chemistry to provide radiolabeled compounds.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

For compounds of Formulae (I), (II), (III), (IV), and (VI), the following preferred embodiments are noted.

Preferably Ar, optionally substituted, is selected from the group consisting of: phenyl, furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, pyridinyl, pyridinyl-N-oxide, pyrazinyl, pyrimidinyl, and pyridazinyl. More preferably, Ar, optionally substituted, is selected from the group consisting of phenyl, furan-3-yl, thiophen-2-yl, and thiophen-3-yl.

In other preferred embodiments, Ar is selected from the group consisting of phenyl, 4-methoxyphenyl, 2-methylphenyl, 3-methylphenyl, 4-methylphenyl, 4-ethylphenyl, 4-isopropylphenyl, 4-tert-butylphenyl, 2-chlorophenyl, 3-chlorophenyl, 4-chlorophenyl, 2-fluorophenyl, 3-fluorophenyl, 4-fluorophenyl, 4-trifluoromethylphenyl, 4-trifluoromethoxyphenyl, 4-cyanophenyl, 4-acetylphenyl, 3,4-difluorophenyl, 3,4-dichlorophenyl, 2,4-dichlorophenyl, 4-nitrophenyl, 3-fluoro-4-chlorophenyl, 4-dimethylaminophenyl, 4-carbamoylphenyl, 4-fluoro-3-methylphenyl, furan-3-yl, thiophen-2-yl, thiophen-3-yl, and 4-tetrazolylphenyl. In further preferred embodiments, Ar is phenyl, optionally substituted with halo. In still further preferred embodiments, Ar is 4-fluorophenyl.

Preferably, ALK, optionally substituted, is selected from the group consisting of methyl, ethyl, propyl, isopropyl, butyl, isobutyl, sec-butyl, tert-butyl, pentyl, isopentyl, hexyl, heptyl, octyl, cyclopropyl, cyclobutyl, cyclopentyl, cyclohexyl, cycloheptyl, cyclooctyl, phenyl, —$CH_2$—CYC, and —$CH_2CH_2$—CYC.

In further preferred embodiments, ALK is selected from the group consisting of methyl, trifluoroethyl, methoxycarbonylmethyl, methylcarbamoylmethyl, ethyl, propyl, 3-methoxycarbonylpropyl, 3-carboxypropyl, butyl, tert-butyl, 4-hydroxybutyl, 4-methoxycarbonylbutyl, 4-carboxybutyl, pentyl, 5-hydroxypentyl, 1-ethylpropyl, 2-ethylpropyl, 2-ethylbutyl, isopropyl, but-3-enyl, isobutyl, 3-methylbutyl, 2-dimethylaminoethyl, 2-cyanoethyl, cyclopropyl, cyclobutyl, cyclopentyl, 3,3-dimethylcyclopentyl, cyclohexyl, 4-methylcyclohexyl, cycloheptyl, cyclooctyl, phenyl, 3-chlorophenyl, 3-fluorophenyl, 2-chlorophenyl, 3-trifluoromethylphenyl, 4-chlorophenyl, —$CH_2$—CYC, and —$CH_2CH_2$—CYC, wherein CYC, optionally substituted, is selected from the group consisting of phenyl, naphthyl, furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, pyridinyl, pyridinyl-N-oxide, pyrazinyl, pyrimidinyl, pyridazinyl, cyclopropyl, cyclobutyl, cyclopentyl, cyclohexyl, cycloheptyl, and cyclooctyl. In still further preferred embodiments, ALK is isopropyl or cyclopentyl.

In additional preferred embodiments, CYC, optionally substituted, is selected from the group consisting of phenyl, pyridyl, and cyclohexyl, thiophen-2-yl, and furan-2-yl.

In further preferred embodiments, CYC is selected from the group consisting of phenyl, 2-methoxyphenyl, 2-methylphenyl, 4-methylphenyl, 2-trifluoro-methylphenyl, 3,4-difluorophenyl, 2,4-difluorophenyl, 2,6-difluorophenyl, 3,4,5-trimethoxyphenyl, 4-methoxy-3-fluorophenyl, thiophen-2-yl, 5-chlorothiophen-2-yl, 2-hydroxyphenyl, 4-hydroxy-2-methylphenyl, 4-hydroxy-3-fluorophenyl, benzo[1,3]dioxol-4 or 5-yl, 5-carboxyethyl-furan-2-yl, naphthalen-1-yl, and cyclohexyl.

In preferred embodiments, $R^2$ is a tert-butoxycarbonyl (Boc) or benzyloxycarbonyl (Cbz) group.

In preferred embodiments, $P^1$ and $P^2$ are both methyl or are taken together to form —(CH$_2$)$_2$—.

In preferred embodiments, the compound of Formula (I) is selected from the group consisting of:

3-(4-Chloro-phenyl)-2-methyl-2,4,5,6,7,8-hexahydro-1,2,6-triaza-azulene;
3-(4-Chloro-phenyl)-2-ethyl-2,4,5,6,7,8-hexahydro-1,2,6-triaza-azulene;
3-(4-Chloro-phenyl)-2-propyl-2,4,5,6,7,8-hexahydro-1,2,6-triaza-azulene;
2-Butyl-3-(4-chloro-phenyl)-2,4,5,6,7,8-hexahydro-1,2,6-triaza-azulene;
3-(4-Chloro-phenyl)-2-(2-cyclohexyl-ethyl)-2,4,5,6,7,8-hexahydro-1,2,6-triaza-azulene;
3-(4-Chloro-phenyl)-2-phenethyl-2,4,5,6,7,8-hexahydro-1,2,6-triaza-azulene;
5-[3-(4-Chloro-phenyl)-5,6,7,8-tetrahydro-4H-1,2,6-triaza-azulen-2-yl]-pentanoic acid methyl ester;
5-[3-(4-Chloro-phenyl)-5,6,7,8-tetrahydro-4H-1,2,6-triaza-azulen-2-yl]-pentanoic acid;
5-[3-(4-Chloro-phenyl)-5,6,7,8-tetrahydro-4H-1,2,6-triaza-azulen-2-yl]-pentan-1-ol;
4-[3-(4-Chloro-phenyl)-5,6,7,8-tetrahydro-4H-1,2,6-triaza-azulen-2-yl]-butyric acid methyl ester;
4-[3-(4-Chloro-phenyl)-5,6,7,8-tetrahydro-4H-1,2,6-triaza-azulen-2-yl]-butyric acid;
4-[3-(4-Chloro-phenyl)-5,6,7,8-tetrahydro-4H-1,2,6-triaza-azulen-2-yl]-butan-1-ol;
3-(4-Chloro-phenyl)-2-(3,4-difluoro-benzyl)-2,4,5,6,7,8-hexahydro-1,2,6-triaza-azulene;
3-(4-Chloro-phenyl)-2-(4-methyl-benzyl)-2,4,5,6,7,8-hexahydro-1,2,6-triaza-azulene;
3-(4-Chloro-phenyl)-2-(3-fluoro-4-methoxy-benzyl)-2,4,5,6,7,8-hexahydro-1,2,6-triaza-azulene;
3-(4-Chloro-phenyl)-2-cyclohexylmethyl-2,4,5,6,7,8-hexahydro-1,2,6-triaza-azulene;
3-(4-Chloro-phenyl)-2-(2-methyl-benzyl)-2,4,5,6,7,8-hexahydro-1,2,6-triaza-azulene;
2-Benzyl-3-(4-chloro-phenyl)-2,4,5,6,7,8-hexahydro-1,2,6-triaza-azulene;
3-(4-Chloro-phenyl)-2-(2,4-difluoro-benzyl)-2,4,5,6,7,8-hexahydro-1,2,6-triaza-azulene;
5-[3-(4-Chloro-phenyl)-5,6,7,8-tetrahydro-4H-1,2,6-triaza-azulen-2-ylmethyl]-furan-2-carboxylic acid ethyl ester;
3-(4-Chloro-phenyl)-2-isobutyl-2,4,5,6,7,8-hexahydro-1,2,6-triaza-azulene;
3-(4-Chloro-phenyl)-2-(2-methoxy-benzyl)-2,4,5,6,7,8-hexahydro-1,2,6-triaza-azulene;
2-Benzyl-3-phenyl-2,4,5,6,7,8-hexahydro-1,2,6-triaza-azulene;
3-(4-Chloro-phenyl)-2-thiophen-2-ylmethyl-2,4,5,6,7,8-hexahydro-1,2,6-triaza-azulene;
3-(4-Chloro-phenyl)-2-(5-chloro-thiophen-2-ylmethyl)-2,4,5,6,7,8-hexahydro-1,2,6-triaza-azulene;
3-(4-Chloro-phenyl)-2-(2,6-difluoro-benzyl)-2,4,5,6,7,8-hexahydro-1,2,6-triaza-azulene;
3-(4-Chloro-phenyl)-2-(2-trifluoromethyl-benzyl)-2,4,5,6,7,8-hexahydro-1,2,6-triaza-azulene;
3-(4-Chloro-phenyl)-2-(2-ethyl-butyl)-2,4,5,6,7,8-hexahydro-1,2,6-triaza-azulene;
2-Benzo[1,3]dioxol-5-ylmethyl-3-(4-chloro-phenyl)-2,4,5,6,7,8-hexahydro-1,2,6-triaza-azulene;
3-(4-Chloro-phenyl)-2-naphthalen-1-ylmethyl-2,4,5,6,7,8-hexahydro-1,2,6-triaza-azulene;
3-(4-Chloro-phenyl)-2-(3,4,5-trimethoxy-benzyl)-2,4,5,6,7,8-hexahydro-1,2,6-triaza-azulene;
2-(3,4-Bis-benzyloxy-benzyl)-3-(4-chloro-phenyl)-2,4,5,6,7,8-hexahydro-1,2,6-triaza-azulene;
4-[3-(4-Chloro-phenyl)-5,6,7,8-tetrahydro-4H-1,2,6-triaza-azulen-2-ylmethyl]-2-fluoro-phenol;
4-[3-(4-Chloro-phenyl)-5,6,7,8-tetrahydro-4H-1,2,6-triaza-azulen-2-ylmethyl]-3-methyl-phenol;
2-[3-(4-Chloro-phenyl)-5,6,7,8-tetrahydro-4H-1,2,6-triaza-azulen-2-ylmethyl]-phenol;
2,3-Diphenyl-2,4,5,6,7,8-hexahydro-1,2,6-triaza-azulene;
2-Cyclohexyl-3-phenyl-2,4,5,6,7,8-hexahydro-1,2,6-triaza-azulene;
3-(4-Chloro-phenyl)-2-cyclohexyl-2,4,5,6,7,8-hexahydro-1,2,6-triaza-azulene;
2-Cyclohexyl-3-(4-trifluoromethyl-phenyl)-2,4,5,6,7,8-hexahydro-1,2,6-triaza-azulene;
2-Cyclopentyl-3-phenyl-2,4,5,6,7,8-hexahydro-1,2,6-triaza-azulene;
3-(4-Chloro-phenyl)-2-cyclopentyl-2,4,5,6,7,8-hexahydro-1,2,6-triaza-azulene;
2-Cyclopentyl-3-(4-fluoro-phenyl)-2,4,5,6,7,8-hexahydro-1,2,6-triaza-azulene;
2-(1-Ethyl-propyl)-3-(3-fluoro-phenyl)-2,4,5,6,7,8-hexahydro-1,2,6-triaza-azulene;
2-(1-Ethyl-propyl)-3-(4-fluoro-phenyl)-2,4,5,6,7,8-hexahydro-1,2,6-triaza-azulene;
2-(1-Ethyl-propyl)-3-thiophen-3-yl-2,4,5,6,7,8-hexahydro-1,2,6-triaza-azulene;
2-(1-Ethyl-propyl)-3-phenyl-2,4,5,6,7,8-hexahydro-1,2,6-triaza-azulene;
3-(4-Chloro-phenyl)-2-(2,2,2-trifluoro-ethyl)-2,4,5,6,7,8-hexahydro-1,2,6-triaza-azulene;
2-(2,2,2-Trifluoro-ethyl)-3-(4-trifluoromethyl-phenyl)-2,4,5,6,7,8-hexahydro-1,2,6-triaza-azulene;
2-Isopropyl-3-phenyl-2,4,5,6,7,8-hexahydro-1,2,6-triaza-azulene;
3-(4-Fluoro-phenyl)-2-isopropyl-2,4,5,6,7,8-hexahydro-1,2,6-triaza-azulene;
2-(1-Ethyl-propyl)-3-thiophen-2-yl-2,4,5,6,7,8-hexahydro-1,2,6-triaza-azulene;
2-Cyclopentyl-3-thiophen-3-yl-2,4,5,6,7,8-hexahydro-1,2,6-triaza-azulene;
2-Ethyl-3-phenyl-2,4,5,6,7,8-hexahydro-1,2,6-triaza-azulene;
2-Ethyl-3-(4-fluoro-phenyl)-2,4,5,6,7,8-hexahydro-1,2,6-triaza-azulene;
2-Ethyl-3-thiophen-2-yl-2,4,5,6,7,8-hexahydro-1,2,6-triaza-azulene;
2-(3-Chloro-phenyl)-3-phenyl-2,4,5,6,7,8-hexahydro-1,2,6-triaza-azulene;
2-(3-Fluoro-phenyl)-3-phenyl-2,4,5,6,7,8-hexahydro-1,2,6-triaza-azulene;

2-(2-Chloro-phenyl)-3-phenyl-2,4,5,6,7,8-hexahydro-1,2,6-triaza-azulene;
2-Phenyl-3-thiophen-2-yl-2,4,5,6,7,8-hexahydro-1,2,6-triaza-azulene;
3-(4-Fluoro-phenyl)-2-phenyl-2,4,5,6,7,8-hexahydro-1,2,6-triaza-azulene;
3-(4-Chloro-phenyl)-2-phenyl-2,4,5,6,7,8-hexahydro-1,2,6-triaza-azulene;
3-(3-Chloro-phenyl)-2-phenyl-2,4,5,6,7,8-hexahydro-1,2,6-triaza-azulene;
2-Phenyl-3-p-tolyl-2,4,5,6,7,8-hexahydro-1,2,6-triaza-azulene;
3-Phenyl-2-(3-trifluoromethyl-phenyl)-2,4,5,6,7,8-hexahydro-1,2,6-triaza-azulene;
3-(4-Methoxy-phenyl)-2-phenyl-2,4,5,6,7,8-hexahydro-1,2,6-triaza-azulene;
2-(4-Chloro-phenyl)-3-phenyl-2,4,5,6,7,8-hexahydro-1,2,6-triaza-azulene;
2-Isopropyl-3-p-tolyl-2,4,5,6,7,8-hexahydro-1,2,6-triaza-azulene;
3-(4-Ethyl-phenyl)-2-isopropyl-2,4,5,6,7,8-hexahydro-1,2,6-triaza-azulene;
3-(4-Chloro-phenyl)-2-isopropyl-2,4,5,6,7,8-hexahydro-1,2,6-triaza-azulene;
4-(2-Isopropyl-2,4,5,6,7,8-hexahydro-1,2,6-triaza-azulen-3-yl)-benzonitrile;
2-Isopropyl-3-(4-trifluoromethyl-phenyl)-2,4,5,6,7,8-hexahydro-1,2,6-triaza-azulene;
2-Ethyl-3-p-tolyl-2,4,5,6,7,8-hexahydro-1,2,6-triaza-azulene;
2-tert-Butyl-3-phenyl-2,4,5,6,7,8-hexahydro-1,2,6-triaza-azulene;
2-tert-Butyl-3-(4-fluoro-phenyl)-2,4,5,6,7,8-hexahydro-1,2,6-triaza-azulene;
2-Cyclopentyl-3-p-tolyl-2,4,5,6,7,8-hexahydro-1,2,6-triaza-azulene;
2-Cyclopentyl-3-(4-trifluoromethyl-phenyl)-2,4,5,6,7,8-hexahydro-1,2,6-triaza-azulene;
3-(3-Chloro-phenyl)-2-cyclopentyl-2,4,5,6,7,8-hexahydro-1,2,6-triaza-azulene;
2-Cyclopentyl-3-(4-methoxy-phenyl)-2,4,5,6,7,8-hexahydro-1,2,6-triaza-azulene;
2-(3,3-Dimethyl-cyclopentyl)-3-phenyl-2,4,5,6,7,8-hexahydro-1,2,6-triaza-azulene;
2-(3,3-Dimethyl-cyclopentyl)-3-(4-fluoro-phenyl-2,4,5,6,7,8-hexahydro-1,2,6-triaza-azulene;
3-(4-Chloro-phenyl)-2-(3,3-dimethyl-cyclopentyl)-2,4,5,6,7,8-hexahydro-1,2,6-triaza-azulene;
2-Cyclohexyl-3-(4-fluoro-phenyl)-2,4,5,6,7,8-hexahydro-1,2,6-triaza-azulene;
2-Cyclohexyl-3-(3,4-difluoro-phenyl)-2,4,5,6,7,8-hexahydro-1,2,6-triaza-azulene;
2-Cyclohexyl-3-p-tolyl-2,4,5,6,7,8-hexahydro-1,2,6-triaza-azulene;
2-Cyclohexyl-3-(4-methoxy-phenyl)-2,4,5,6,7,8-hexahydro-1,2,6-triaza-azulene;
4-(2-Cyclohexyl-2,4,5,6,7,8-hexahydro-1,2,6-triaza-azulen-3-yl)-benzonitrile;
3-(3-Chloro-phenyl)-2-cyclohexyl-2,4,5,6,7,8-hexahydro-1,2,6-triaza-azulene;
2-Cyclopentyl-3-furan-3-yl-2,4,5,6,7,8-hexahydro-1,2,6-triaza-azulene;
2-Cyclopentyl-3-thiophen-2-yl-2,4,5,6,7,8-hexahydro-1,2,6-triaza-azulene;
2-tert-Butyl-3-thiophen-3-yl-2,4,5,6,7,8-hexahydro-1,2,6-triaza-azulene;
2-tert-Butyl-3-furan-3-yl-2,4,5,6,7,8-hexahydro-1,2,6-triaza-azulene;
2-Cyclopentyl-3-(3,4-difluoro-phenyl)-2,4,5,6,7,8-hexahydro-1,2,6-triaza-azulene;
3-(4-Chloro-phenyl)-2-cyclobutyl-2,4,5,6,7,8-hexahydro-1,2,6-triaza-azulene;
2-tert-Butyl-3-thiophen-2-yl-2,4,5,6,7,8-hexahydro-1,2,6-triaza-azulene;
3-(3-Chloro-4-fluoro-phenyl)-2-cyclopentyl-2,4,5,6,7,8-hexahydro-1,2,6-triaza-azulene;
2-Isopropyl-3-(4-methoxy-phenyl)-2,4,5,6,7,8-hexahydro-1,2,6-triaza-azulene;
2-Isopropyl-3-(4-trifluoromethoxy-phenyl)-2,4,5,6,7,8-hexahydro-1,2,6-triaza-azulene;
2-Isopropyl-3-(4-isopropyl-phenyl)-2,4,5,6,7,8-hexahydro-1,2,6-triaza-azulene;
3-(4-tert-Butyl-phenyl)-2-isopropyl-2,4,5,6,7,8-hexahydro-1,2,6-triaza-azulene;
2-Isopropyl-3-m-tolyl-2,4,5,6,7,8-hexahydro-1,2,6-triaza-azulene;
2-Isopropyl-3-o-tolyl-2,4,5,6,7,8-hexahydro-1,2,6-triaza-azulene;
3-(3,4-Dichloro-phenyl)-2-isopropyl-2,4,5,6,7,8-hexahydro-1,2,6-triaza-azulene;
2-Benzyl-3-(4-fluoro-phenyl)-2,4,5,6,7,8-hexahydro-1,2,6-triaza-azulene;
2-Isopropyl-3-thiophen-2-yl-2,4,5,6,7,8-hexahydro-1,2,6-triaza-azulene;
3-(2-Chloro-phenyl)-2-isopropyl-2,4,5,6,7,8-hexahydro-1,2,6-triaza-azulene;
1-[4-(2-Isopropyl-2,4,5,6,7,8-hexahydro-1,2,6-triaza-azulen-3-yl)-phenyl]-ethanone;
2-Isopropyl-3-(4-nitro-phenyl)-2,4,5,6,7,8-hexahydro-1,2,6-triaza-azulene;
2-Ethyl-3-(4-ethyl-phenyl)-2,4,5,6,7,8-hexahydro-1,2,6-triaza-azulene;
4-(2-Ethyl-2,4,5,6,7,8-hexahydro-1,2,6-triaza-azulen-3-yl)-benzonitrile;
2-Ethyl-3-(4-isopropyl-phenyl)-2,4,5,6,7,8-hexahydro-1,2,6-triaza-azulene;
2-Ethyl-3-(4-methoxy-phenyl)-2,4,5,6,7,8-hexahydro-1,2,6-triaza-azulene;
2-Ethyl-3-(4-trifluoromethyl-phenyl)-2,4,5,6,7,8-hexahydro-1,2,6-triaza-azulene;
2-Ethyl-3-o-tolyl-2,4,5,6,7,8-hexahydro-1,2,6-triaza-azulene;
3-(2-Chloro-phenyl)-2-ethyl-2,4,5,6,7,8-hexahydro-1,2,6-triaza-azulene;
2-Ethyl-3-(2-fluoro-phenyl)-2,4,5,6,7,8-hexahydro-1,2,6-triaza-azulene;
3-(2,4-Dichloro-phenyl)-2-isopropyl-2,4,5,6,7,8-hexahydro-1,2,6-triaza-azulene;
[4-(2-Ethyl-2,4,5,6,7,8-hexahydro-1,2,6-triaza-azulen-3-yl)-phenyl]-dimethyl-amine;
3-(4'-Chloro-biphenyl-4-yl)-2-(2,2,2-trifluoro-ethyl)-2,4,5,6,7,8-hexahydro-1,2,6-triaza-azulene;
3-(4'-Chloro-biphenyl-4-yl)-2-cyclopentyl-2,4,5,6,7,8-hexahydro-1,2,6-triaza-azulene;
2-Cyclobutyl-3-phenyl-2,4,5,6,7,8-hexahydro-1,2,6-triaza-azulene;
2-Cyclobutyl-3-(4-fluoro-phenyl)-2,4,5,6,7,8-hexahydro-1,2,6-triaza-azulene;
2-Cyclobutyl-3-p-tolyl-2,4,5,6,7,8-hexahydro-1,2,6-triaza-azulene;
2-Cyclobutyl-3-(4-trifluoromethyl-phenyl)-2,4,5,6,7,8-hexahydro-1,2,6-triaza-azulene;

4-(2-Cyclobutyl-2,4,5,6,7,8-hexahydro-1,2,6-triaza-azulen-3-yl)-benzonitrile
2-Cyclopropyl-3-phenyl-2,4,5,6,7,8-hexahydro-1,2,6-triaza-azulene;
2-Cyclopropyl-3-(4-fluoro-phenyl)-2,4,5,6,7,8-hexahydro-1,2,6-triaza-azulene;
2-(1-Ethyl-propyl)-3-(4-fluoro-3-methyl-phenyl)-2,4,5,6,7,8-hexahydro-1,2,6-triaza-azulene;
2-Cyclopropyl-3-p-tolyl-2,4,5,6,7,8-hexahydro-1,2,6-triaza-azulene;
2-Cyclopropyl-3-thiophen-3-yl-2,4,5,6,7,8-hexahydro-1,2,6-triaza-azulene;
4-(2-Cyclopropyl-2,4,5,6,7,8-hexahydro-1,2,6-triaza-azulen-3-yl)-benzonitrile;
2-sec-Butyl-3-phenyl-2,4,5,6,7,8-hexahydro-1,2,6-triaza-azulene;
2-sec-Butyl-3-(4-fluoro-phenyl)-2,4,5,6,7,8-hexahydro-1,2,6-triaza-azulene;
2-sec-Butyl-3-p-tolyl-2,4,5,6,7,8-hexahydro-1,2,6-triaza-azulene;
2-sec-Butyl-3-(4-trifluoromethyl-phenyl)-2,4,5,6,7,8-hexahydro-1,2,6-triaza-azulene;
4-(2-Isopropyl-2,4,5,6,7,8-hexahydro-1,2,6-triaza-azulen-3-yl)-benzamide;
2-Isopropyl-3-[4-(1H-tetrazol-5-yl)-phenyl]-2,4,5,6,7,8-hexahydro-1,2,6-triaza-azulene;
3-(4-Chloro-phenyl)-2-pyridin-2-ylmethyl-1,4,5,6,7,8-hexahydro-1,2,6-triaza-azulene;
3-[3-(4-Chloro-phenyl)-5,6,7,8-tetrahydro-4H-1,2,6-triaza-azulen-2-yl]-propionitrile;
3-(4-Chloro-phenyl)-2-cycloheptyl-2,4,5,6,7,8-hexahydro-1,2,6-triaza-azulene;
3-(4-Chloro-phenyl)-2-cyclooctyl-2,4,5,6,7,8-hexahydro-1,2,6-triaza-azulene; and
3-(4-Chloro-phenyl)-2-(4-methyl-cyclohexyl)-2,4,5,6,7,8-hexahydro-1,2,6-triaza-azulene;
and pharmaceutically acceptable salts thereof.

In further preferred embodiments, the compound of Formula (I) is 3-(4-fluoro-phenyl)-2-isopropyl-2,4,5,6,7,8-hexahydro-1,2,6-triaza-azulene or 2-cyclopentyl-3-(4-fluoro-phenyl)-2,4,5,6,7,8-hexahydro-1,2,6-triaza-azulene, or a pharmaceutically acceptable salt thereof.

In preferred embodiments, the compound of formula (IV) is {2-[4-[1,3]dioxolan-2-ylmethyl-5-(4-fluoro-phenyl)-1-isopropyl-1H-pyrazol-3-yl]-ethyl}-carbamic acid benzyl ester or {2-[4-[1,3]dioxolan-2-ylmethyl-5-(4-fluoro-phenyl)-1-cyclopentyl-1H-pyrazol-3-yl]-ethyl}-carbamic acid benzyl ester.

In preferred embodiments, the compound of formula (II) is [3-(ALK-hydrazono)-propyl]-carbamic acid benzyl ester, where ALK is defined as above. In further preferred embodiments, the compound of formula (II) is [3-(isopropyl-hydrazono)-propyl]-carbamic acid benzyl ester or [3-(cyclopentyl-hydrazono)-propyl]-carbamic acid benzyl ester.

Preferably, the compound of formula (III) is 2-[3-(4-fluoro-phenyl)-2-nitro-allyl]-[1,3]dioxolane.

Methods of the invention will now be described by reference to illustrative synthetic schemes and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Suitable starting materials may be obtained from commercial sources or synthesized by methods known to one skilled in the art. Unless otherwise specified, the variables are as defined above in reference to Formula (I).

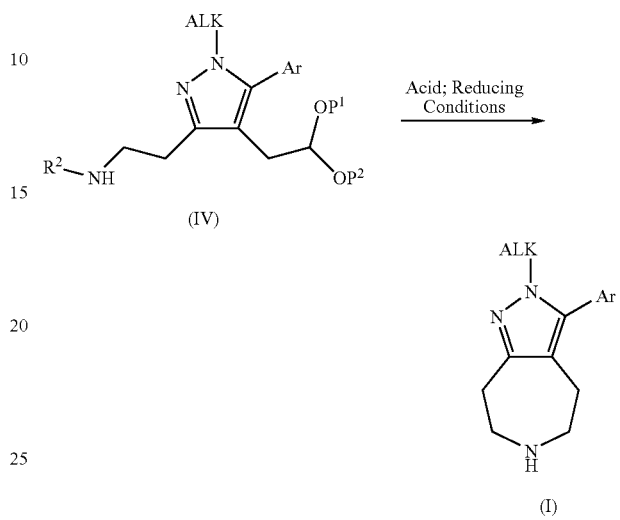

A method of making a compound of Formula (I) according to the present invention comprises reacting a compound of formula (IV) with an acid under reducing conditions, in a non-basic organic solvent, at a temperature between about room temperature and the reflux temperature of the solvent, to give the compound of Formula (I), as depicted in Scheme A.

Preferred conditions include those where deprotection of the $R^2$ protecting group, deprotection of $P^1$ and $P^2$, cyclization, and reduction occur in the same reaction step. Preferably, a compound of formula (IV) is reacted with an acid (such as TFA, HCl, $H_2SO_4$, and the like), and i) a reducing agent (such as $Et_3SiH$, $NaB(OAc)_3H$, $NaCNBH_3$, and the like) or ii) a hydrogen donor (such as $H_2$, cyclohexene, ammonium formate, formic acid, an the like) and a catalyst (such as palladium on carbon (Pd/C), palladium black (Pd-black), $Pd(OH)_2$, platinum on carbon, Raney nickel, ruthenium black, and the like), in a non-basic organic solvent, to form the compound of Formula (I). Examples of a non-basic organic solvent include an alcohol solvent (such as t-amyl alcohol, isopropanol, ethanol, methanol, and the like), an ethereal solvent (such as THF, MTBE, and the like), an aromatic solvent (such as toluene and the like), an acidic solvent (such as AcOH, TFA, and the like), water, EtOAc, and the like, or a mixture thereof. In further preferred embodiments, the acid is HCl at a concentration less than 6 M. In still further preferred embodiments, the acid is TFA, the reducing agent is $Et_3SiH$, and the non-basic organic solvent is TFA. In other preferred embodiments, the acid is 3 M HCl, the hydrogen donor is $H_2$, the catalyst is Pd/C, and the non-basic organic solvent is t-amyl alcohol.

Methods of making a compound of Formula (I) also include those wherein removal of $P^1$ and $P^2$ and cyclization occur in the presence of an acid in a first step, and reducing conditions are employed in a subsequent step. Thus, the method of making a compound of Formula (I) comprises reacting a compound of formula (VI):

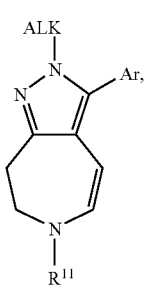

(VI)

where $R^{11}$ is H or Cbz; and Ar and ALK are as previously defined, with i) a reducing agent or $NaBH_4$, or ii) a hydrogen donor and a catalyst; in a non-basic organic solvent, at a temperature between about room temperature and reflux temperature of the solvent, to form the compound of Formula (I). In preferred embodiments, the hydrogen donor is $H_2$, the catalyst is Pd/C, and the non-basic organic solvent is isopropanol. In further preferred embodiments, the reducing agent is $Et_3SiH$ and the non-basic organic solvent is TFA. In preferred embodiments, the compound of formula (VI) is 3-(4-fluoro-phenyl)-2-isopropyl-7,8-dihydro-2H-1,2,6-triaza-azulene-6-carboxylic acid benzyl ester.

The method further comprises reacting a compound of formula (IV) with an acid, in a non-basic organic solvent, at a temperature between about room temperature and reflux temperature of the solvent, to form a compound of formula (VI). In preferred embodiments, the acid is TFA and the non-basic organic solvent is water. The non-basic organic solvent may be the same or different in the first and subsequent steps.

The present invention is further directed to compounds of formula (VI), which are useful in the preparation of compounds of Formula (I).

SCHEME B

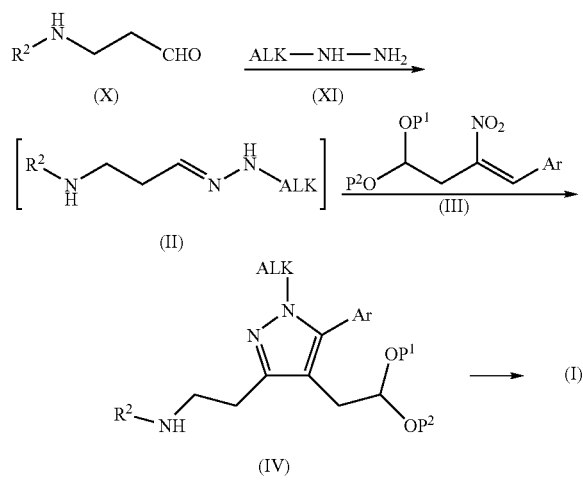

A method of making a compound of Formula (I) further comprises reacting a hydrazone of formula (II) with a nitroolefin of formula (III), in an organic solvent, in the presence of oxygen, at a temperature between about room temperature and the reflux temperature of the solvent, to form the compound of formula (IV), as depicted in Scheme B. Preferably, the compound of formula (IV) is formed with a regioisomeric excess of at least about 90% with respect to a compound of formula (IVa):

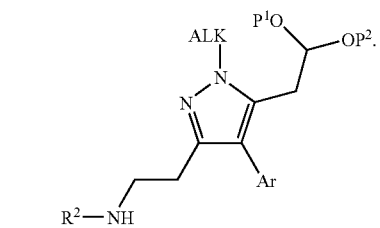

(IVa)

More preferably, the compound of formula (IV) is formed with a regioisomeric excess of at least about 95%. Examples of an organic solvent include an alcohol solvent (such as methanol, ethanol, isopropanol, and the like), an alcohol/water mixture (such as methanol/water, ethanol/water, and the like), a tertiary amine solvent (such as $Et_3N$, $iPr_2NEt$, N-methylmorpholine, and the like), AcOH, DCM, THF, DMF, pyridine, and the like, or a mixture thereof. In further preferred embodiments, the organic solvent is $Et_3N$, THF, or pyridine. In still further preferred embodiments, the organic solvent is isopropanol, THF, or DMF, further comprising at least about one equivalent of $Et_3N$ or pyridine. In still further preferred embodiments, the organic solvent is isopropanol, THF, or DMF, further comprising at least about four equivalents of $Et_3N$.

The method of making a compound of Formula (I) further comprises mixing an aldehyde of formula (X) with a hydrazine of formula (XI), in a solvent selected from a tertiary amine base, pyridine, and a non-basic organic solvent, further comprising at least one equivalent of a tertiary amine base, at a temperature between about room temperature and the reflux temperature of the solvent, to form a compound of formula (II), as depicted in Scheme B. The non-basic organic solvent may be the same or different as in Scheme A. In preferred embodiments, the tertiary amine base is $Et_3N$, $iPr_2NEt$, or N-methylmorpholine. In other preferred embodiments, the non-basic organic solvent is an alcohol solvent (such as methanol, ethanol, or isopropanol), an alcohol/water mixture (such as ethanol/water), or a polar solvent (such as THF or DMF), or a mixture thereof.

Conversion of a compound of formula (X) to a compound of formula (IV) is optionally accomplished in a single reaction vessel. The method of making a compound of Formula (I) therefore comprises: 1) mixing an aldehyde of formula (X) with a hydrazine of formula (XI) in a solvent selected from a tertiary amine base, pyridine, and a non-basic organic solvent further comprising at least one equivalent of a tertiary amine base, to form an organic mixture; and 2) adding a nitroolefin of formula (III) to the organic mixture to form the compound of formula (IV). In preferred embodiments, the tertiary amine base is $Et_3N$, $iPr_2NEt$, or N-methylmorpholine. In other preferred embodiments, the non-basic organic solvent is an alcohol solvent (such as methanol, ethanol, or isopropanol), alcohol/water mixtures (such as ethanol/water), or a polar solvent (such as THF or DMF), or a mixture thereof. In further preferred embodiments, the organic solvent is isopropanol or DMF, further comprising at least one equivalent of $Et_3N$. In still further preferred embodiments, the organic solvent is isopropanol or DMF, further comprising at least four equivalents of $Et_3N$.

SCHEME C

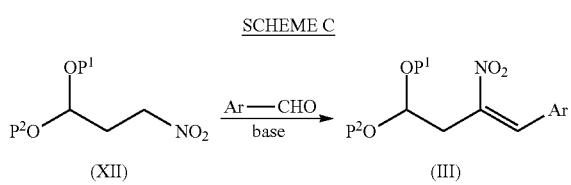

A method of making a compound of Formula (I) further comprises reacting a nitroalkane of formula (XII) with an aldehyde Ar—CHO, in the presence of an amine base, in an aromatic organic solvent, at a temperature between about room temperature and the reflux temperature of the solvent, to form a nitroolefin of formula (III), as depicted in Scheme C. In preferred embodiments, the amine base is $Et_3N$, $iPr_2NEt$, pyridine, morpholine, pyrrolidine, or piperidine, or a mixture thereof. In further preferred embodiments, the aromatic organic solvent is toluene, benzene, or xylene, or a mixture thereof. In still further preferred embodiments, water is removed from the reaction with a Dean-Stark trap. In other preferred embodiments, the amine base is piperidine and the aromatic organic solvent is toluene.

SCHEME D

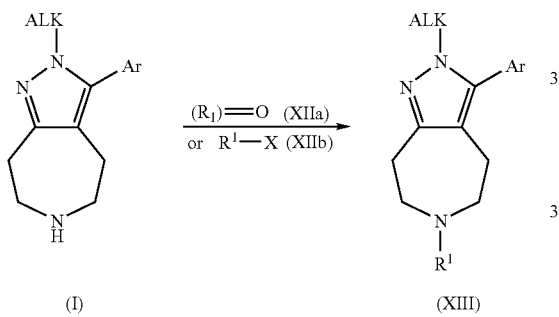

As depicted in Scheme D, a compound of Formula (I) is optionally processed into a compound of formula (XIII), where $R^1$ is —$C_{1-7}$alkyl or —$C_{1-3}$alkyl-phenyl, by alkylation or reductive amination protocols such as those described in Intl. Pat. Appl. Publ. WO2005040169 (See, e.g., Scheme 3 and Examples 208, 259, 260, 269-272, 287, 289-291, 302). Such compounds are modulators of serotonin receptors, and are useful in methods for treating or preventing diseases and conditions mediated by serotonin receptors, particularly the $5HT_7$ and/or $5HT_2$ receptor subtypes. Said compounds were disclosed in Intl. Pat. Appl. Publ. WO2005040169 (See, e.g., Scheme 3 and Examples 208, 259, 260, 269-272, 287, 289-291, 302). The method of the present invention thus further comprises reacting a compound of Formula (I) with a compound of formula (XIIa) or a compound of formula (XIIb), wherein X is a suitable leaving group such as Cl, Br, I, p-toluenesulfonyloxy, methanesulfonyloxy, and the like, to provide a compound of formula (XIII). In preferred embodiments, $R^1$ is methyl, ethyl, isopropyl, benzyl, phenethyl, or phenpropyl. In preferred embodiments, the compound of formula (XIII) is selected from the group consisting of: 6-methyl-2,3-diphenyl-2,4,5,6,7,8-hexahydro-1,2,6-triaza-azulene; 3-(4-fluoro-phenyl)-2-isopropyl-6-methyl-2,4,5,6,7,8-hexahydro-1,2,6-triaza-azulene; 3-(4-fluoro-phenyl)-2,6-diisopropyl-2,4,5,6,7,8-hexahydro-1,2,6-triaza-azulene; 6-benzyl-3-(4-fluoro-phenyl)-2-isopropyl-2,4,5,6,7,8-hexahydro-1,2,6-triaza-azulene; 3-(4-fluoro-phenyl)-2-isopropyl-6-(3-phenyl-propyl)-2,4,5,6,7,8-hexahydro-1,2,6-triaza-azulene; 3-(4-fluoro-phenyl)-2-isopropyl-6-phenethyl-2,4,5,6,7,8-hexahydro-1,2,6-triaza-azulene; and 2-cyclopentyl-3-(4-fluoro-phenyl)-6-methyl-2,4,5,6,7,8-hexahydro-1,2,6-triaza-azulene.

SCHEME E

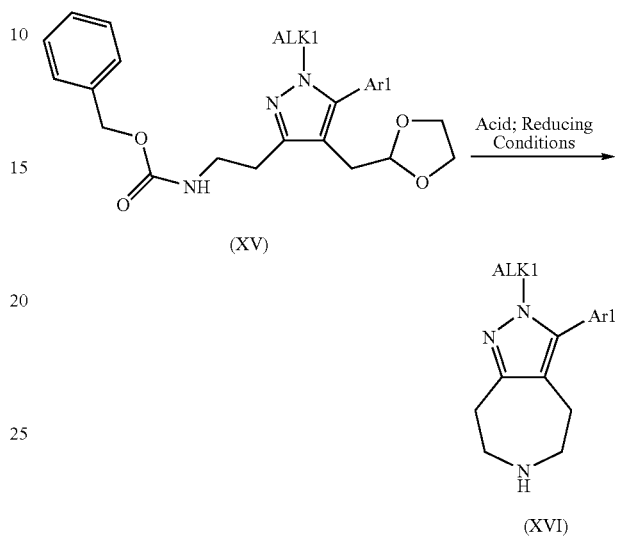

A method of making a compound of Formula (XVI) according to the present invention comprises reacting a compound of formula (XV) with an acid under reducing conditions, in a non-basic organic solvent, at a temperature between about room temperature and the reflux temperature of the solvent, to give the compound of Formula (XVI) as depicted in Scheme E, where ALK1 and Ar1 are defined as for Formula (XVI) and (XV) above.

Preferred conditions include those where deprotection of the Cbz group, deprotection of the dioxolane group, cyclization, and reduction occur in the same reaction step. Preferably, a compound of formula (XV) is reacted with an acid (such as TFA, HCl, $H_2SO_4$, and the like), and i) a reducing agent (such as $Et_3SiH$, $NaB(OAc)_3H$, $NaCNBH_3$, and the like) or ii) a hydrogen donor (such as $H_2$, cyclohexene, ammonium formate, formic acid, and the like) and a catalyst (such as palladium on carbon (Pd/C), palladium black (Pd-black), $Pd(OH)_2$, platinum on carbon, Raney nickel, ruthenium black, and the like), in a non-basic organic solvent, to form the compound of Formula (XVI). Examples of a non-basic organic solvent include an alcohol solvent (such as t-amyl alcohol, isopropanol, ethanol, methanol, and the like), an ethereal solvent (such as THF, MTBE, and the like), an aromatic solvent (such as toluene and the like), an acidic solvent (such as AcOH, TFA, and the like), water, EtOAc, and the like, or a mixture thereof. In further preferred embodiments, the acid is HCl at a concentration less than 6 M. In still further preferred embodiments, the acid is TFA, the reducing agent is $Et_3SiH$, and the non-basic organic solvent is TFA. In other preferred embodiments, the acid is 3 M HCl, the hydrogen donor is $H_2$, the catalyst is Pd/C, and the non-basic organic solvent is t-amyl alcohol.

Methods of making a compound of Formula (XVI) also include those wherein removal of the dioxolane and cyclization occur in the presence of an acid in a first step, and reducing conditions are employed in a subsequent step. Thus, the method of making a compound of Formula (XVI) comprises reacting a compound of formula (XVII):

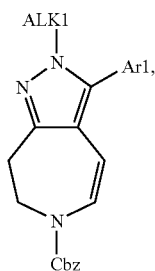

(XVII)

where Ar1 and ALK1 are as previously defined, with i) a reducing agent or NaBH₄, or ii) a hydrogen donor and a catalyst; in a non-basic organic solvent, at a temperature between about room temperature and reflux temperature of the solvent, to form the compound of Formula (XVI). In preferred embodiments, the hydrogen donor is H₂, the catalyst is Pd/C, and the non-basic organic solvent is isopropanol. In further preferred embodiments, the reducing agent is Et₃SiH, and the non-basic organic solvent is TFA. In preferred embodiments, the compound of formula (XVII) is 3-(4-fluoro-phenyl)-2-isopropyl-7,8-dihydro-2H-1,2,6-triaza-azulene-6-carboxylic acid benzyl ester.

The method further comprises reacting a compound of formula (XV) with an acid, in a non-basic solvent, at a temperature between about room temperature and reflux temperature of the solvent, to form a compound of formula (XVII). In preferred embodiments, the acid is TFA and the non-basic organic solvent is water. In the processes of the present invention, the non-basic organic solvent may be the same or different in the first and subsequent steps.

The present invention is further directed to compounds of formula (XVII), which are useful in the preparation of compounds of Formula (XVI).

SCHEME F

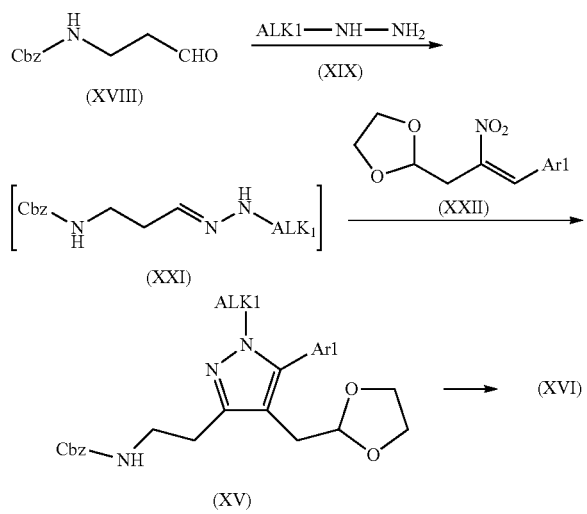

A method of making a compound of Formula (XVI) further comprises reacting a hydrazone of formula (XXI) with a nitroolefin of formula (XXII), in an organic solvent, in the presence of oxygen, at a temperature between about room temperature and the reflux temperature of the solvent, to form the compound of formula (XV), as depicted in Scheme F. Preferably, the compound of formula (XV) is formed with a regioisomeric excess of at least about 90%. More preferably, the compound of formula (XV) is formed with a regioisomeric excess of at least about 95%. Examples of an organic solvent include an alcohol solvent (such as methanol, ethanol, isopropanol, and the like), an alcohol/water mixture (such as methanol/water, ethanol/water, and the like), a tertiary amine solvent (such as Et₃N, iPr₂NEt, N-methylmorpholine, and the like), AcOH, DCM, THF, DMF, pyridine, and the like, or a mixture thereof. In further preferred embodiments, the organic solvent is Et₃N, THF, or pyridine. In still further preferred embodiments, the organic solvent is isopropanol, THF, or DMF, further comprising at least about one equivalent of Et₃N or pyridine. In still further preferred embodiments, the organic solvent is isopropanol, THF, or DMF, further comprising at least about four equivalents of Et₃N.

The method of making a compound of Formula (XVI) further comprises mixing an aldehyde of formula (XVIII) with a hydrazine of formula (XIX), in a solvent selected from a tertiary amine base, pyridine, and a non-basic organic solvent further comprising at least one equivalent of a tertiary amine base, at a temperature between about room temperature and the reflux temperature of the solvent, to form a compound of formula (XXI), as depicted in Scheme F. The non-basic organic solvent may be the same or different as in Scheme E. In preferred embodiments, the tertiary amine base is Et₃N, iPr₂NEt, or N-methylmorpholine. In preferred embodiments, the tertiary amine base is Et₃N, iPr₂NEt, or N-methylmorpholine. In other preferred embodiments, the non-basic organic solvent is an alcohol solvent (such as methanol, ethanol, or isopropanol), an alcohol/water mixture (such as ethanol/water), or a polar solvent (such as THF or DMF), or a mixture thereof.

Conversion of a compound of formula (XVIII) to a compound of Formula (XVI) is optionally accomplished in a single reaction vessel. The method of making a compound of Formula (XVI) therefore comprises: 1) mixing an aldehyde of formula (XVIII) with a hydrazine of formula (XIX) in a solvent selected from a tertiary amine base, pyridine, and a non-basic organic solvent further comprising at least one equivalent of a tertiary amine base, to form an organic mixture; and 2) adding a nitroolefin of formula (XXII) to the organic mixture to form the compound of formula (XV). In preferred embodiments, the tertiary amine base is Et₃N, iPr₂NEt, or N-methylmorpholine. In other preferred embodiments, the non-basic organic solvent is an alcohol solvent (such as methanol, ethanol, or isopropanol), alcohol/water mixtures (such as ethanol/water), or a polar solvent (such as THF or DMF), or a mixture thereof. In further preferred embodiments, the organic solvent is isopropanol or DMF, further comprising at least one equivalent of Et₃N. In still further preferred embodiments, the organic solvent is isopropanol or DMF, further comprising at least four equivalents of Et₃N.

SCHEME G

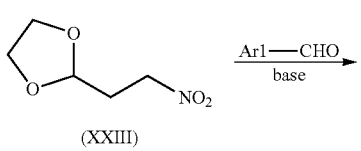

(XXIII)

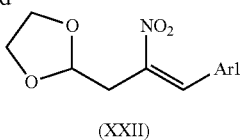

(XXII)

A method of making a compound of Formula (XVI) further comprises reacting a nitroalkane of formula (XXIII) with an aldehyde Ar1-CHO, in the presence of an amine base, in an aromatic organic solvent, at a temperature between about room temperature and the reflux temperature of the solvent, to form a nitroolefin of formula (XXII), as depicted in Scheme G. In preferred embodiments, the amine base is Et$_3$N, iPr$_2$NEt, pyridine, morpholine, pyrrolidine, or piperidine, or a mixture thereof. In further preferred embodiments, the aromatic organic solvent is toluene, benzene, or xylene, or a mixture thereof. In still further preferred embodiments, water is removed from the reaction with a Dean-Stark trap. In other preferred embodiments, the amine base is piperidine and the aromatic organic solvent is toluene.

SCHEME H

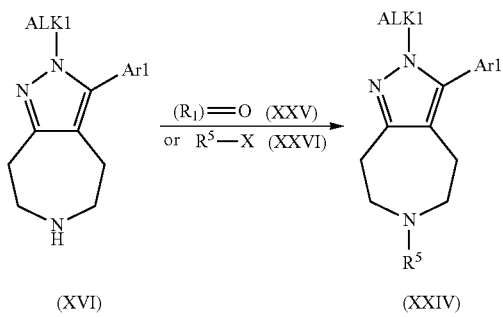

As depicted in Scheme H, a compound of Formula (XVI) is optionally processed into a compound of formula (XXIV), where R$^5$ is —C$_{1-7}$alkyl or —C$_{1-3}$alkyl-phenyl, by alkylation or reductive amination protocols such as those described in Intl. Pat. Appl. Publ. WO2005040169 (See, e.g., Scheme 3 and Examples 208, 259, 260, 269-272, 287, 289-291, 302). The method of the present invention thus further comprises reacting a compound of Formula (XVI) with a compound of formula (XXV) or a compound of formula (XXVI), wherein X is a suitable leaving group such as Cl, Br, I, p-toluenesulfonyloxy, methanesulfonyloxy, and the like, to provide a compound of formula (XXIV). In preferred embodiments, R$^5$ is methyl, ethyl, isopropyl, benzyl, phenethyl, and phenpropyl. In further preferred embodiments, the compound of formula (XXIV) is selected from the group consisting of: 3-(4-fluoro-phenyl)-2-isopropyl-6-methyl-2,4,5,6,7,8-hexahydro-1,2,6-triaza-azulene; 3-(4-fluoro-phenyl)-2,6-diisopropyl-2,4,5,6,7,8-hexahydro-1,2,6-triaza-azulene; 6-benzyl-3-(4-fluoro-phenyl)-2-isopropyl-2,4,5,6,7,8-hexahydro-1,2,6-triaza-azulene; 3-(4-fluoro-phenyl)-2-isopropyl-6-(3-phenyl-propyl)-2,4,5,6,7,8-hexahydro-1,2,6-triaza-azulene; 3-(4-fluoro-phenyl)-2-isopropyl-6-phenethyl-2,4,5,6,7,8-hexahydro-1,2,6-triaza-azulene; and 2-cyclopentyl-3-(4-fluoro-phenyl)-6-methyl-2,4,5,6,7,8-hexahydro-1,2,6-triaza-azulene.

Compounds of Formula (I) are converted to their corresponding salts using methods known to those skilled in the art. For example, an amine of Formula (I) is treated with TFA, HCl, or citric acid, in a solvent such as methanol, to provide the corresponding salt form.

Compounds prepared according to the methods of the invention may be obtained as single enantiomers, diastereomers, or regioisomers by enantio-, diastero-, or regiospecific synthesis, or by resolution. Compounds prepared according to the methods of the invention may also be obtained as racemic (1:1) or non-racemic (not 1:1) mixtures of enantiomers, or as mixtures of diastereomers, regioisomers, or atropisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric, diastereomeric, or atropisomeric mixtures are obtained, single isomers may be separated using conventional methods such as chromatography or crystallization.

The following examples are provided to further illustrate aspects of the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions are "dried," they are generally dried over a drying agent such as Na$_2$SO$_4$ or MgSO$_4$. Where mixtures, solutions, and extracts were "concentrated", they were typically concentrated on a rotary evaporator under reduced pressure.

Thin-layer chromatography was performed using Merck silica gel 60 F$_{254}$ 2.5 cm×7.5 cm 250 µm or 5.0 cm×10.0 cm 250 µm pre-coated silica gel plates. Preparative thin-layer chromatography was performed using EM Science silica gel 60 F$_{254}$ 20 cm×20 cm 0.5 mm pre-coated plates with a 20 cm×4 cm concentrating zone.

Normal-phase flash column chromatography (FCC) was performed on silica gel (SiO$_2$) eluting with EtOAc/hexanes, unless otherwise noted.

Reversed-phase HPLC was performed on a Hewlett Packard HPLC Series 1100, with a Agilent ZORBAX® Eclipse XDP-C8 (5 µm, 4.6×150 mm) column. Detection was done at λ=220 and 254 nm. The gradient was 1 to 99% acetonitrile/water (0.05% TFA) over 8.0 min with a flow rate of 1 mL/min.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration).

Chemical names were generated using ChemDraw Version 6.0.2 (CambridgeSoft, Cambridge, Mass.).

Example 1

(3-Oxo-propyl)-carbamic acid benzyl ester

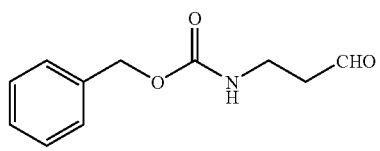

A solution of (3-hydroxy-propyl)-carbamic acid benzyl ester (100 g, 478 mmol) and 2,2,6,6-tetramethyl-1-piperidinyloxy, free radical (TEMPO; 7.5 g, 48 mmol) in DCM (1 L) was treated with (diacetoxyiodo)benzene, PhI(OAc)$_2$, (170 g, 528 mmol) in three portions. After 18 h at rt, the mixture was slowly quenched with saturated aqueous (satd. aq.) NaHCO$_3$. The organic layer was separated, washed with satd. aq. NaCl (500 mL), dried (Na$_2$SO$_4$), and concentrated. The residue was purified by FCC to give a solid, which was stirred in 1:1 Et$_2$O/hexanes for 2 h. The solid was collected by filtration. Successive iterations were combined to provide the title compound as a white solid. $^1$H NMR (400 MHz, CDCl$_3$): 9.81 (s, 1H), 7.36-7.31 (m, 5H), 5.14 (br s, 1H), 5.08 (s, 2H), 3.49 (q, J=6.0, 2H), 2.75 (t, J=5.7, 2H).

Example 2

2-(2-Nitro-ethyl)-[1,3]dioxolane

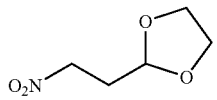

Step A. 3-Nitro-propionaldehyde. The title compound was prepared as described by Griesser, H. et al. Org. Synth. 2000, 77, 236-243.
Step B. In a flask fitted with a Dean-Stark trap and reflux condenser, a solution of 3-nitro-propionaldehyde (138 g, 1.34 mol) in toluene (1 L) was treated with ethylene glycol (83 g, 1.34 mol) and p-toluenesulfonic acid monohydrate (5.0 g, 26 mmol). The mixture was heated at reflux, open to air, for 4 h, and then cooled to rt. A black residue was removed by paper filtration. The filtrate was washed with satd. aq. NaHCO$_3$ (250 mL) and brine (3×100 mL). Charcoal and MgSO$_4$ were added, and the resulting suspension was stirred for 1 h. Filtration and concentration of the filtrate gave the title compound. $^1$H NMR (400 MHz, CDCl$_3$): 5.03 (t, J=3.6, 1H), 4.50 (t, J=6.8, 2H), 4.05-3.90 (m, 2H), 3.90-3.80 (m, 2H), 2.44 (td, J=6.8, 3.6, 2H).

Example 3

(Z)-2-[3-(4-Fluoro-phenyl)-2-nitro-allyl]-[1,3]dioxolane

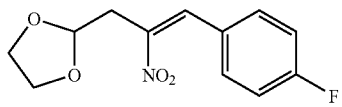

In a flask equipped with a Dean-Stark trap and a reflux condenser, a solution of 2-(2-nitro-ethyl)-[1,3]dioxolane (162.5 g, 1.1 mol) in toluene (1.2 L) was treated with 4-fluorobenzaldehyde (124 g, 1.0 mol) followed by piperidine (15 mL, 0.15 mol). The solution was heated at reflux under N$_2$ for 16 h, then was cooled to rt and washed with water (2×300 mL) and satd. aq. NaCl (2×300 mL). Charcoal and MgSO$_4$ were added, and the suspension was stirred for 1 h. Filtration and concentration of the filtrate provided the title compound, which was used in the next reaction without further purification. $^1$H NMR (400 MHz, CDCl$_3$): 8.15 (s, 1H), 7.70-7.65 (m, 2H), 7.18-7.10 (m, 2H), 5.23 (t, J=4.5, 1H), 4.10-3.80 (m, 4H), 3.26 (d, J=4.5, 2H). The (Z)-olefin geometry was confirmed by nuclear Overhauser effect (NOE) studies (Stott et al. J. Magn. Reson. 1997, 125, 302-324) with a mixing time of 0.8 sec. When proton at 8.15 ppm was selectively inverted, NOE was observed at 3.25 ppm and 7.65 ppm.

Example 4

[3-(Isopropyl-hydrazono)-propyl]-carbamic acid benzyl ester

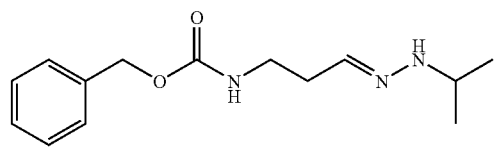

To a stirred solution of isopropylhydrazine hydrochloride (92.4 g, 0.84 mol) and (3-oxo-propyl)-carbamic acid benzyl ester (173 g, 0.84 mol) in isopropyl alcohol (1.7 L) was added Et$_3$N (140 mL, 1.0 mol) over 20 min. The resulting slurry was heated at reflux for 3 h, and then was cooled to rt and concentrated. The residue was partitioned between EtOAc (700 mL) and water (700 mL). The organic layer was washed with water (3×500 mL), satd. aq. NaCl (300 mL), dried (MgSO$_4$), and concentrated to afford the title compound. The crude product was used in next reaction without purification. MS (ESI): exact mass calcd. for C$_{14}$H$_{21}$N$_3$O$_2$, 263.16; m/z found, 264.3 [M+H]$^+$. $^1$H NMR (400 MHz, CDCl$_3$): 7.36-7.25 (m, 5H), 7.02 (t, J=4.5, 1H), 5.10 (br s, 1H), 5.09 (s, 2H), 3.45-3.34 (m, 3H), 2.40-2.34 (m, 2H), 1.11 (d, J=6.4, 6H).

Example 5

{2-[4-[1,3]Dioxolan-2-ylmethyl-5-(4-fluoro-phenyl)-1-isopropyl-1H-pyrazol-3-yl]-ethyl}-carbamic acid benzyl ester

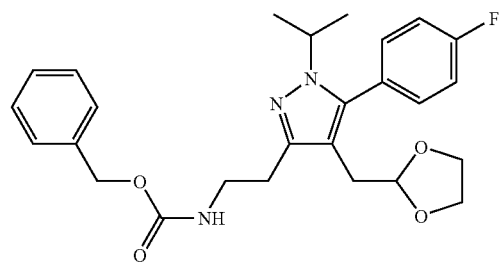

To a solution of [3-(isopropyl-hydrazono)-propyl]-carbamic acid benzyl ester (216 g, 0.82 mol) in Et$_3$N (1 L) was added 2-[3-(4-fluoro-phenyl)-2-nitro-allyl]-[1,3]dioxolane (173 g, 0.68 mol) over 20 min. The mixture was stirred at rt, open to air, for 2 days (d). The mixture was concentrated, diluted with water (500 mL), and extracted with EtOAc (1.2 L). The organic layer was washed with water (3×500 mL) and satd. aq. NaCl (500 mL), dried (MgSO$_4$), and filtered through a short pad of SiO$_2$ (ca. 200 g). The filtrate was concentrated to give an orange, viscous oil (330 g). The oil was dried under vacuum for 2 d, giving an orange solid. The solid was slurried in Et$_2$O (350 mL) and triturated with hexanes (600 mL). The mixture was stirred at rt for 30 min, and the solid was collected by filtration and dried in a vacuum oven at 40° C. to give the title compound. MS (ESI): exact mass calcd. for $C_{26}H_{30}FN_3O_4$, 467.22; m/z found, 468.4 [M+H]+. $^1$H NMR (500 MHz, CDCl$_3$): 7.35-7.25 (m, 7H), 7.18-7.10 (m, 2H), 5.82 (s, 1H), 5.09 (s, 2H), 4.75 (t, J=4.8, 1H), 4.22-4.14 (m, 1H), 3.85-3.79 (m, 2H), 3.79-3.70 (m, 2H), 3.58 (q, J=6.1, 2H), 2.85 (t, J=6.1, 2H), 2.59 (d, J=4.8, 2H), 1.35 (d, J=6.6, 6H).

Alternative Procedure 1

A solution of [3-(isopropyl-hydrazono)-propyl]-carbamic acid benzyl ester (60.0 mg, 0.228 mmol) and 2-[3-(4-fluoro-phenyl)-2-nitro-allyl]-[1,3]dioxolane (54.0 mg, 0.213 mmol) in THF (2 mL) was stirred at rt for 3 days. The mixture was treated with additional [3-(isopropyl-hydrazono)-propyl]-carbamic acid benzyl ester (1.4 equiv.) and was stirred at 60° C. for 18 h. Additional [3-(isopropyl-hydrazono)-propyl]-carbamic acid benzyl ester (2.1 equiv.) was added, and the mixture was stirred at 60° C. for 18 h. The mixture was concentrated to oil and the residue was purified by FCC to give the title compound.

Alternative Procedure 2

A solution of [3-(isopropyl-hydrazono)-propyl]-carbamic acid benzyl ester (1.0 mg, 3.8 mmol), 2-[3-(4-fluoro-phenyl)-2-nitro-allyl]-[1,3]dioxolane (0.96 mg, 3.8 mmol), and Et$_3$N (1.53 g, 15.2 mmol) in THF (40 mL) was stirred at 60° C. for 3 days. The mixture was cooled to rt, concentrated, and the residue purified by FCC to give the title compound.

Alternative Procedure 3

A solution of [3-(isopropyl-hydrazono)-propyl]-carbamic acid benzyl ester (0.5 g, 1.9 mmol) and 2-[3-(4-fluoro-phenyl)-2-nitro-allyl]-[1,3]dioxolane (0.48 g, 1.9 mmol) in pyridine (20 mL) was stirred at rt for 2 days. The mixture was cooled to rt, concentrated, and the residue purified by FCC to give the title compound.

Example 6

{2-[4-[1,3]Dioxolan-2-ylmethyl-5-(4-fluoro-phenyl)-1-isopropyl-1H-pyrazol-3-yl]-ethyl}-carbamic acid benzyl ester (One-step process)

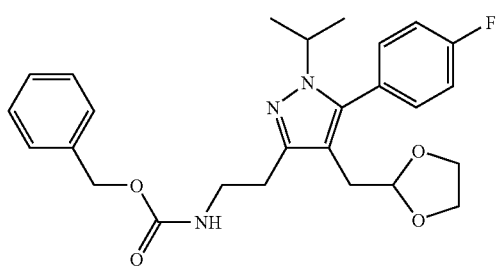

A solution of isopropylhydrazine hydrochloride (1.07 g, 9.7 mmol) and (3-oxo-propyl)-carbamic acid benzyl ester (2.0 g, 9.7 mmol) in Et$_3$N (20 mL) was heated at 60° C. After 1 h, 2-[3-(4-fluoro-phenyl)-2-nitro-allyl]-[1,3]dioxolane (2.2 g, 8.7 mmol) was added. After 16 h at 60° C., the mixture was cooled to rt and concentrated. The residue was partitioned between EtOAc and water. The organic layer was separated, dried (MgSO$_4$), and concentrated. Purification by FCC gave the title compound.

Alternative Procedure 1

A solution of isopropylhydrazine hydrochloride (0.53 g, 4.8 mmol), (3-oxo-propyl)-carbamic acid benzyl ester (1.0 g, 4.8 mmol), and Et$_3$N (1.94 g, 192 mmol) in DMF (20 mL) was stirred at rt for 18 h. The solution was treated with 2-[3-(4-fluoro-phenyl)-2-nitro-allyl]-[1,3]dioxolane (1.02 g, 3.95 mmol) and stirred at 60° C. for 18 h. The mixture was cooled to rt and concentrated. The residue was partitioned between EtOAc and water. The organic layer was separated, dried (MgSO$_4$), and concentrated. Purification by FCC gave the title compound.

Alternative Procedure 2

A solution of isopropylhydrazine hydrochloride (1.06 g, 9.6 mmol), (3-oxo-propyl)-carbamic acid benzyl ester (2.0 g, 9.6 mmol), and Et$_3$N (3.9 g, 38.4 mmol) in isopropanol (30 mL) was heated to reflux. After 3 h, the solution was treated with 2-[3-(4-fluoro-phenyl)-2-nitro-allyl]-[1,3]dioxolane (2.2 g, 8.7 mmol) and stirred at 60° C. for 18 h. The mixture was cooled to rt and concentrated. The residue was partitioned between EtOAc and water. The organic layer was separated, dried (MgSO$_4$), and concentrated. Purification by FCC gave the title compound.

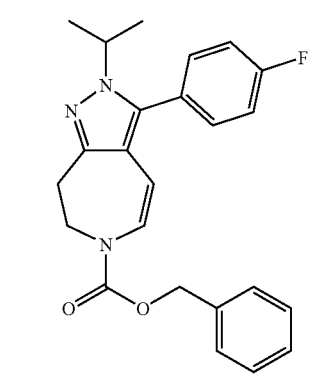

Example 7

3-(4-Fluoro-phenyl)-2-isopropyl-7,8-dihydro-2H-1,2,6-triaza-azulene-6-carboxylic acid benzyl ester A solution of {2-[4-[1,3]dioxolan-2-ylmethyl-5-(4-fluoro-phenyl)-1-isopropyl-1H-pyrazol-3-yl]-ethyl}-carbamic acid benzyl ester (0.5 g, 1.1 mmol) in TFA (10 mL) and water (2 mL) was heated at reflux for 2 h. The mixture was concentrated and the residue was purified by FCC to provide the title compound. HPLC: R$_t$=11.00 min. MS (ESI): mass calcd. for $C_{24}H_{24}FN_3O_2$, 405.19; m/z found, 406.3 [M+H]+.

Example 8

3-(4-Fluoro-phenyl)-2-isopropyl-2,4,5,6,7,8-hexahydro-1,2,6-triaza-azulene

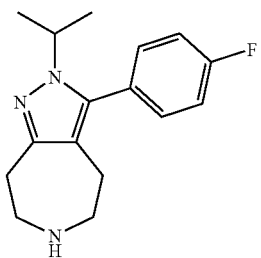

To a 2.2 L Parr hydrogenation flask was added {2-[4-[1,3]dioxolan-2-ylmethyl-5-(4-fluoro-phenyl)-1-isopropyl-1H-pyrazol-3-yl]-ethyl}-carbamic acid benzyl ester (90.0 g, 0.193 mol), t-amyl alcohol (910 mL), and 3 N HCl (190 mL, 0.570 mol). The flask was charged with $N_{2(g)}$ and 10% Pd/C (22.2 g) was added. The reaction mixture was hydrogenated at 40 psi and at 45° C. for 18 h. The mixture was filtered through acid-treated, low metal filter paper. The filtrate was concentrated to oil, diluted with water (500 mL), and washed with EtOAc (3×250 mL). The aqueous mixture was cooled to 0° C. and basified to pH 13-14 by the addition of KOH pellets. The aqueous solution was extracted with EtOAc (3×250 mL). The combined organic layers were filtered through acid-treated filter paper. The filtrate was dried ($Na_2SO_4$) and concentrated to give the title compound. MS (ESI): exact mass calcd. for $C_{16}H_{20}FN_3$, 273.16; m/z found, 274.3 [M+H]$^+$. $^1$H NMR (400 MHz, CDCl$_3$): 7.25-7.20 (m, 2H), 7.18-7.13 (t, J=8.6, 2H), 4.28-4.21 (sept, J=6.6, 1H), 3.04-3.01 (m, 2H), 2.94-2.88 (m, 4H), 2.46 (t, J=5.2, 2H), 1.40 (d, J=6.6, 6H).

Alternative Procedure 1

A solution of {2-[4-[1,3]dioxolan-2-ylmethyl-5-(4-fluoro-phenyl)-1-isopropyl-1H-pyrazol-3-yl]-ethyl}-carbamic acid benzyl ester (1.0 g, 2.1 mmol) in TFA (10 mL) was treated with Et$_3$SiH (2.5 mL, 21 mmol). After 16 h at 50° C., the solution was concentrated and the residue was purified by FCC to afford the title compound.

Alternative Procedure 2

A mixture of 3-(4-fluoro-phenyl)-2-isopropyl-7,8-dihydro-2H-1,2,6-triaza-azulene-6-carboxylic acid benzyl ester (0.2 g, 0.49 mmol) and 10% Pd/C (20 mg) in isopropanol (20 mL) was subjected to H$_2$ (45 psi) at rt for 16 h. The mixture was filtered and the filtrate was concentrated. The residue was purified by FCC to give the title compound.

Example 9

3-(4-Fluoro-phenyl)-2-isopropyl-2,4,5,6,7,8-hexahydro-1,2,6-triaza-azulene, citrate salt

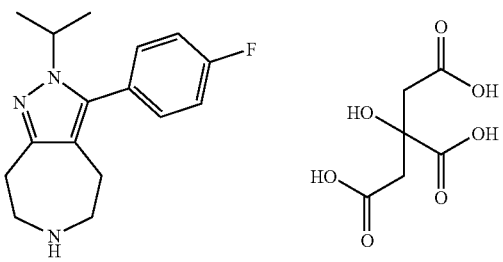

A solution of 3-(4-fluoro-phenyl)-2-isopropyl-2,4,5,6,7,8-hexahydro-1,2,6-triaza-azulene (160.0 g, 0.585 mol) in methanol (1.2 L) was treated with a solution of citric acid (123.7 g, 0.644 mol) in methanol (500 mL). The solution was stirred for 18 h at rt, then was diluted with EtOAc (1 L) and stirred another 24 h. The resulting precipitate was filtered, washed with 4:1 EtOAc/methanol, and dried to give a first crop of the title compound. The filtrate was concentrated and basified to pH 13-14 with 3 N KOH. The aqueous solution was extracted with EtOAc (3×200 mL). The combined organic layers were dried (Na$_2$SO$_4$) and concentrated to recover 52 g of the free base of the title compound. The free base was diluted with methanol (300 mL) and treated with citric acid (21.5 g, 0.112 mol). The mixture was stirred for 18 h, concentrated to approx. 150 mL, diluted with EtOAc (300 mL), and stirred for 24 h. The resulting precipitate was collected by filtration, washed with 4:1 EtOAc/methanol, and dried, to give a second crop of the title compound. mp 164-166° C. $^1$H NMR (400 MHz, D$_2$O): 7.26-7.23 (m, 2H), 7.18-7.14 (t, J=8.9, 2H), 4.29-4.24 (m, 1H), 3.31-3.29 (t, J=5.3, 2H), 3.18-3.16 (t, J=5.3, 2H), 3.03-3.01 (t, J=5.6, 2H), 2.75 (d, J=15.5, 2H), 2.64 (d, J=15.5, 2H), 2.65-2.63 (m, 2H), 1.21 (d, J=6.7, 6H). Anal. calcd. for C$_{22}$H$_{28}$FN$_3$O$_7$: C, 56.77; H, 6.06; N, 9.03. Found: C, 56.59; H, 6.42; N, 9.04.

Example 10

{2-[1-Cyclopentyl-4-[1,3]dioxolan-2-ylmethyl-5-(4-fluoro-phenyl)-1H-pyrazol-3-yl]-ethyl}-carbamic acid benzyl ester

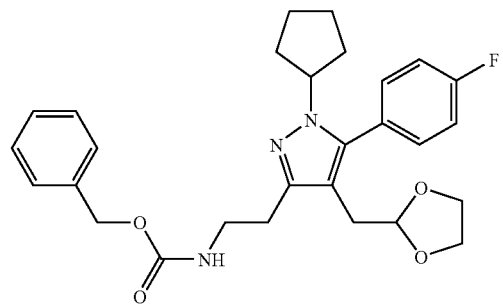

The title compound was prepared in a manner analogous to that described in Examples 1-5, substituting cyclopentylhydrazine in place for isopropylhydrazine in Example 4. MS (ESI): exact mass calcd. for C$_{28}$H$_{32}$FN$_3$O$_4$, 493.24; m/z found, 494.1 [M+H]$^+$. $^1$H NMR (400 MHz, CDCl$_3$): 7.42-7.26 (m, 7H), 7.20-7.10 (m, 2H), 5.92 (s, 1H), 5.11 (s, 2H), 4.76 (t, J=5.2, 1H), 4.30 (sept, J=7.6, 1H), 3.90-3.80 (m, 2H), 3.80-3.70 (m, 2H), 3.58 (q, J=5.6, 2H), 2.85 (t, J=6.0, 2H), 2.60 (d, J=4.8, 2H), 2.10-1.95 (m, 2H), 1.95-1.80 (m, 4H), 1.60-1.45 (m, 2H).

Example 11

2-Cyclopentyl-3-(4-fluoro-phenyl)-2,4,5,6,7,8-hexahydro-1,2,6-triaza-azulene

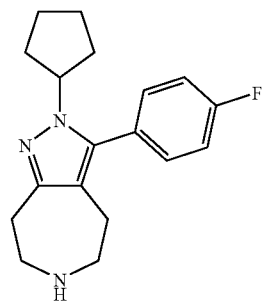

The title compound was prepared from {2-[1-cyclopentyl-4-[1,3]dioxolan-2-ylmethyl-5-(4-fluoro-phenyl)-1H-pyrazol-3-yl]-ethyl}-carbamic acid benzyl ester in a manner analogous to that described in Example 8. MS (ESI): exact mass calcd. for C$_{18}$H$_{22}$FN$_3$, 299.18; m/z found, 300.3 [M+H]$^+$. $^1$H NMR (400 MHz, DMSO-d$_6$): 7.40-7.30 (m, 4H), 4.35 (quint, J=7.6, 1H), 3.00-2.90 (m, 2H), 2.90-2.76 (m, 4H), 2.46-2.40 (m, 2H), 1.96-1.70 (m, 6H), 1.56-1.46 (m, 2H).

While the invention has been illustrated by reference to examples, it is understood that the invention is intended not to be limited to the foregoing detailed description.

What is claimed is:

1. A method of making a compound of Formula (I):

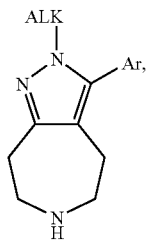

(I)

or an enantiomer, diastereomer, or pharmaceutically acceptable salt thereof;
comprising reacting a compound of formula (IV):

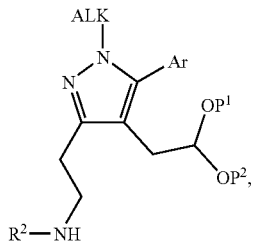

(IV)

with an acid under reducing conditions, in a non-basic organic solvent, at a temperature between about room temperature and the reflux temperature of the solvent, to provide the compound of Formula (I),
wherein
Ar is 4-fluorophenyl;
ALK is isopropyl or cyclopentyl;
$R^2$ is —$CO_2R^{10}$ or a benzyl group unsubstituted or substituted with one or two —$OCH_3$ substituents;
where $R^{10}$ is methyl, ethyl, 2-trimethylsilylethyl, 2-phenylethyl, 1-(1-adamantyl)-1-methylethyl, t-butyl, 1-adamantyl, vinyl, allyl, benzyl, p-methoxybenzyl, p-nitrobenzyl, p-chlorobenzyl, 2,4-dichlorobenzyl, or diphenylmethyl; and
$P^1$ and $P^2$ are each independently —$C_{1-4}$alkyl, or, alternatively, $P^1$ and $P^2$ taken together form —$(CH_2)_{2-3}$—.

2. A method according to claim 1, wherein ALK is isopropyl.

3. A method according to claim 1, wherein ALK is cyclopentyl.

4. A method according to claim 1, wherein the compound of Formula (I) is 3-(4-fluoro-phenyl)-2-isopropyl-2,4,5,6,7,8-hexahydro-1,2,6-triaza-azulene or 2-cyclopentyl-3-(4-fluoro-phenyl)-2,4,5,6,7,8-hexahydro-1,2,6-triaza-azulene, or a pharmaceutically acceptable salt thereof.

5. A method according to claim 1, wherein said pharmaceutically acceptable salt is a citrate salt.

6. A method according to claim 1, wherein said acid is selected from TFA, HCl, or $H_2SO_4$.

7. A method according to claim 1, wherein said reducing conditions comprise a reducing agent selected from $Et_3SiH$, $NaB(OAc)_3H$, or $NaCNBH_3$.

8. A method according to claim 1, wherein said reducing conditions comprise a hydrogen donor selected from $H_2$, cyclohexene, ammonium formate, or formic acid, and a catalyst selected from palladium on carbon, palladium black, $Pd(OH)_2$, platinum on carbon, Raney nickel, or ruthenium black.

9. A method according to claim 1, wherein said non-basic organic solvent is selected from t-amyl alcohol, isopropanol, ethanol, methanol, THF, MTBE, toluene, AcOH, TFA, water, or EtOAc, or a mixture thereof.

10. A method according to claim 6, wherein the acid is HCl at a concentration less than 6 M.

11. A method according to claim 1, wherein said acid is TFA, said reducing agent is $Et_3SiH$, and said non-basic organic solvent is TFA.

12. A method according to claim 8, wherein said acid is 3 M HCl, said hydrogen donor is $H_2$, said catalyst is Pd/C, and said non-basic organic solvent is t-amyl alcohol.

13. A method of making a compound of Formula (I):

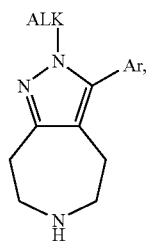

(I)

or an enantiomer, diastereomer, or pharmaceutically acceptable salt thereof;
comprising reacting a compound of formula (VI):

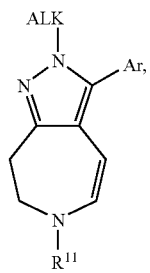

(VI)

with a reducing agent, $NaBH_4$, or a hydrogen donor and a catalyst, in a non-basic organic solvent, at a temperature between about room temperature and reflux temperature of the solvent, to provide the compound of Formula (I),
wherein
Ar is 4-fluorophenyl;
ALK is isopropyl or cyclopentyl; and
$R^{11}$ is H or benzyloxycarbonyl.

14. A method according to claim 13, wherein the hydrogen donor is $H_2$, the catalyst is Pd/C, and the non-basic organic solvent is isopropanol.

15. A method according to claim 13, wherein the reducing agent is $Et_3SiH$ and the non-basic organic solvent is TFA.

16. A method according to claim 13, wherein the compound of formula (VI) is 3-(4-fluoro-phenyl)-2-isopropyl-7,8-dihydro-2H-1,2,6-triaza-azulene-6-carboxylic acid benzyl ester.

17. A method according to claim 13, further comprising reacting a compound of formula (IV):

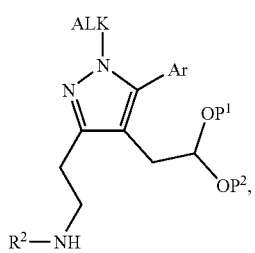
(IV)

with an acid, in a non-basic organic solvent, at a temperature between about room temperature and reflux temperature of the solvent, to form a compound of formula (VI),
wherein
$R^2$ is —$CO_2R^{10}$ or a benzyl group unsubstituted or substituted with one or two —$OCH_3$ substituents;
where $R^{10}$ is methyl, ethyl, 2-trimethylsilylethyl, 2-phenylethyl, 1-(1-adamantyl)-1-methylethyl, t-butyl, 1-adamantyl, vinyl, allyl, benzyl, p-methoxybenzyl, p-nitrobenzyl, p-chlorobenzyl, 2,4-dichlorobenzyl, or diphenylmethyl; and
$P^1$ and $P^2$ are each independently —$C_{1-4}$alkyl, or, alternatively, $P^1$ and $P^2$ taken together form —$(CH_2)_{2-3}$—.

18. A method according to claim 17, wherein the acid is TFA and the non-basic organic solvent is water.

19. A method according to claim 1 or 17, further comprising:
reacting a hydrazone of formula (II):

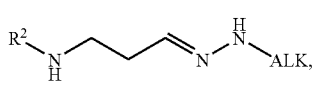
(II)

with a nitroolefin of formula (III):

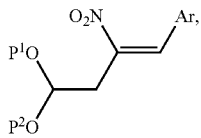
(III)

in the presence of oxygen, in an organic solvent, at a temperature between about room temperature and the reflux temperature of the solvent, to form the compound of formula (IV),

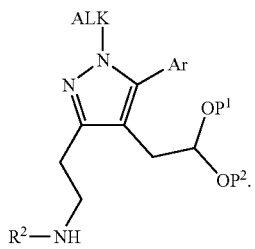
(IV)

20. A method according to claim 19, further comprising:
mixing an aldehyde of formula (X):

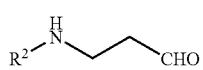
(X)

with a hydrazine of formula (XI):
ALK—NH—$NH_2$ (XI),
in the presence of a tertiary amine base, in a solvent selected from a tertiary amine base, pyridine, or a non-basic organic solvent further comprising at least one equivalent of a tertiary amine base, at a temperature between about room temperature and the reflux temperature of the solvent, to form the compound of formula (II).

21. A method according to claim 19, further comprising:
1) mixing an aldehyde of formula (X)

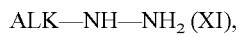
(X)

with a hydrazine of formula (XI)
ALK—NH—$NH_2$ (XI)
in a solvent selected from a tertiary amine base, pyridine, or a non-basic organic solvent further comprising at least one equivalent of a tertiary amine base, to form an organic mixture, and 2) adding a nitroolefin of formula (III)

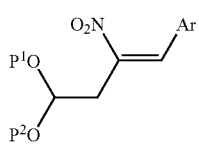
(III)

to the organic mixture to form the compound of formula (IV)

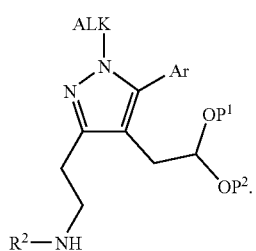
(IV)

* * * * *